US011957592B2

(12) United States Patent
Linder-Ganz et al.

(10) Patent No.: US 11,957,592 B2
(45) Date of Patent: Apr. 16, 2024

(54) MENISCUS PROSTHETIC DEVICES WITH ANTI-MIGRATION OR RADIOPAQUE FEATURES

(71) Applicant: Active Implants LLC, Memphis, TN (US)

(72) Inventors: Eran Linder-Ganz, Tel Aviv (IL); Lex R. Giltaij, Odijk (NL); Richard W. Treharne, Memphis, TN (US); Thomas B. Buford, Laguna Beach, CA (US); Dvora Galli, Lehavot Haviva (IL)

( * ) Notice: Subject to any disclaimer, the term of this patent is extended or adjusted under 35 U.S.C. 154(b) by 38 days.

(21) Appl. No.: 17/942,892

(22) Filed: Sep. 12, 2022

(65) Prior Publication Data

US 2023/0248528 A1 Aug. 10, 2023

Related U.S. Application Data

(60) Continuation of application No. 16/945,150, filed on Jul. 31, 2020, now Pat. No. 11,439,510, which is a (Continued)

(51) Int. Cl.
*A61F 2/38* (2006.01)
*A61B 17/56* (2006.01)
(Continued)

(52) U.S. Cl.
CPC .......... *A61F 2/3872* (2013.01); *A61B 17/562* (2013.01); *A61F 2/30756* (2013.01);
(Continued)

(58) Field of Classification Search
CPC .. A61F 2/3868; A61F 2/3872; A61F 2/30756; A61F 2002/30822; A61B 17/562; A61B 2017/0414
See application file for complete search history.

(56) References Cited

U.S. PATENT DOCUMENTS 3,875,928 A 4/1975 Angelchik
4,052,753 A 10/1977 Dedo
(Continued)

FOREIGN PATENT DOCUMENTS

WO WO-2005069957 A2 * 8/2005 ............... A61F 2/38

OTHER PUBLICATIONS

International Search Report and Written Opinion received in corresponding Patent Cooperation Treaty Application No. PCT/US2014/027124, dated Jul. 24, 2014, 12 pages.

*Primary Examiner* — Javier G Blanco
(74) *Attorney, Agent, or Firm* — Haynes and Boone, LLP

(57) ABSTRACT

A prosthetic device for use as an artificial meniscus is disclosed. The prosthetic device restores stress distribution, stability, and function to the knee joint after removal of the damaged natural meniscus. In some embodiments, the prosthetic device includes an anti-migration feature that inhibits extreme movement within the joint while permitting free floating over a significant range. In one aspect, the anti-migration feature is an enlarged anterior structure or a posterior meniscus remnant engaging channel while in another aspect, the anti-migration feature includes a tethering member. Still further, removable radiopaque features are provided to enhance trialing of the implant prior to final implantation within the joint.

7 Claims, 21 Drawing Sheets

Related U.S. Application Data continuation of application No. 16/153,514, filed on Oct. 5, 2018, now Pat. No. 10,736,749, which is a continuation of application No. 15/789,145, filed on Oct. 20, 2017, now Pat. No. 10,092,408, which is a continuation of application No. 15/135,250, filed on Apr. 21, 2016, now Pat. No. 9,795,488, which is a division of application No. 14/212,330, filed on Mar. 14, 2014, now Pat. No. 9,381,089.

(60) Provisional application No. 61/785,725, filed on Mar. 14, 2013.

(51) Int. Cl.
*A61F 2/30* (2006.01)
*A61B 17/04* (2006.01)
*A61B 17/84* (2006.01)

(52) U.S. Cl.
CPC ..... *A61B 2017/0414* (2013.01); *A61B 17/842* (2013.01); *A61F 2002/3008* (2013.01); *A61F 2002/30578* (2013.01); *A61F 2002/30822* (2013.01); *A61F 2/30965* (2013.01); *A61F 2/3868* (2013.01); *A61F 2250/0098* (2013.01)

(56) References Cited

U.S. PATENT DOCUMENTS

| | | |
|---|---|---|
| 4,344,193 A | 8/1982 | Kenny |
| 4,467,479 A | 8/1984 | Brody |
| 4,502,161 A | 3/1985 | Wall |
| 4,919,667 A * | 4/1990 | Richmond ............ A61F 2/3872 623/905 |
| 6,174,330 B1 | 1/2001 | Stinson |
| 6,206,927 B1 | 3/2001 | Fell et al. |
| 7,291,169 B2 | 11/2007 | Hodorek |
| 7,632,311 B2 | 12/2009 | Seedhom et al. |
| 7,998,205 B2 | 8/2011 | Hagen et al. |
| 8,287,594 B2 | 10/2012 | Cragg et al. |
| 8,361,147 B2 | 1/2013 | Shterling et al. |
| 2003/0036797 A1 | 2/2003 | Malaviya et al. |
| 2003/0060888 A1 | 3/2003 | Fell et al. |
| 2006/0149370 A1 | 7/2006 | Schmieding |
| 2007/0067032 A1 | 3/2007 | Felt et al. |
| 2007/0100450 A1 | 5/2007 | Hodorek |
| 2009/0012615 A1 | 1/2009 | Fell |
| 2009/0259312 A1 | 10/2009 | Shterling et al. |
| 2010/0161054 A1 | 6/2010 | Park et al. |
| 2011/0172768 A1 | 7/2011 | Cragg et al. |
| 2012/0232656 A1 | 9/2012 | Gedet et al. |
| 2013/0190873 A1 | 7/2013 | Mansmann |
| 2013/0304223 A1 * | 11/2013 | Hassler ................ A61F 2/4261 623/21.14 |

* cited by examiner

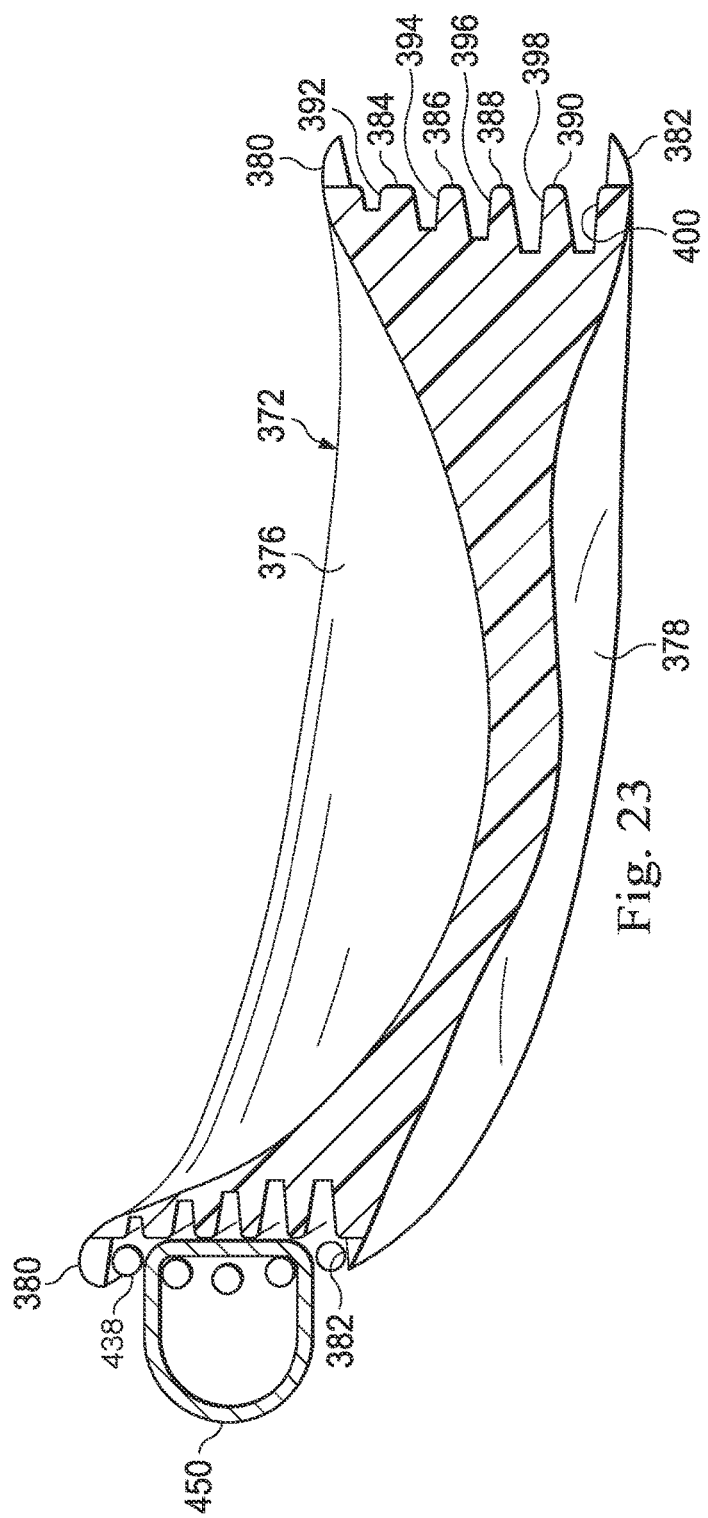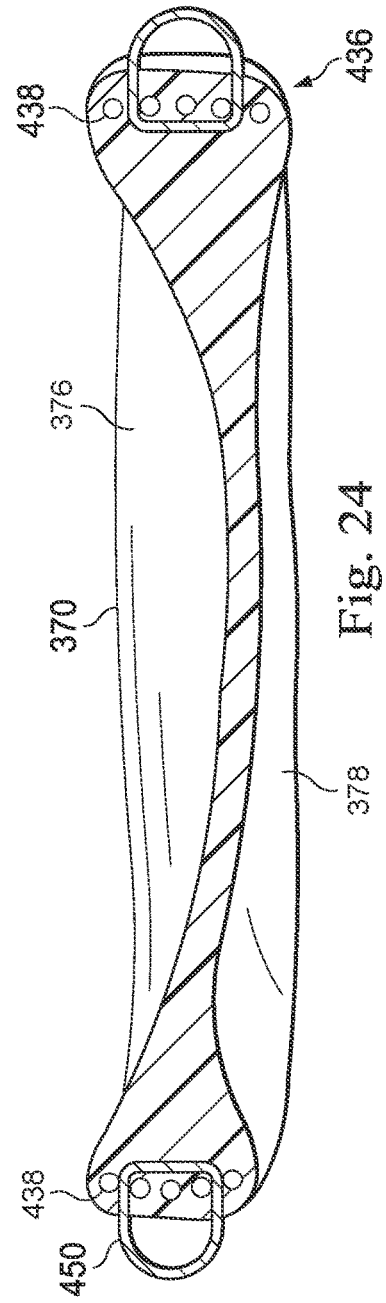

MENISCUS PROSTHETIC DEVICES WITH ANTI-MIGRATION OR RADIOPAQUE FEATURES

CROSS-REFERENCE TO RELATED APPLICATIONS

This application is a continuation of U.S. patent application Ser. No. 16/945,150, filed Jul. 31, 2020, issued as U.S. Pat. No. 11,439,510, which is a continuation of U.S. patent application Ser. No. 16/153,514, filed Oct. 5, 2018, issued as U.S. Pat. No. 10,736,749, which is a continuation of U.S. patent application Ser. No. 15/789,145, filed Oct. 20, 2017, issued as U.S. Pat. No. 10,092,408, which is a continuation of U.S. patent application Ser. No. 15/135,250, filed Apr. 21, 2016, issued as U.S. Pat. No. 9,795,488, which is a division of U.S. patent application Ser. No. 14/212,330, filed Mar. 14, 2014, issued as U.S. Pat. No. 9,381,089, which claims priority to and the benefit of U.S. Provisional Patent Application No. 61/785,725, filed Mar. 14, 2013, the entireties of which are hereby incorporated by reference herein.

BACKGROUND

The present disclosure generally relates to medical prosthetic devices, systems, and methods. More specifically, in some instances the present disclosure relates to prosthetic devices that replace at least part of the functionality of the natural meniscus. Each knee has two menisci, a lateral meniscus and a medial meniscus. Each meniscus is a crescent-shaped fibrocartilaginous tissue attached to the tibia at an anterior and a posterior horn. Damage to the meniscus can cause pain and arthritis. Accordingly, in some instances it is desirable to replace the damaged natural meniscus with a prosthetic device. In some instances the prosthetic devices of the present disclosure are configured to be surgically implanted into a knee joint to replace or augment the natural meniscus. It is important that the prosthetic device be of the appropriate size and functionality for the intended patient. During implantation procedures it can be difficult to evaluate movement of the meniscus replacement device in the knee joint. Still further, in certain patients initial meniscus replacement devices have been expelled from the knee joint or were mis-positioned in the first place. Thus, there is a need for meniscus replacement devices that can be more readily observed during implantation and retained in its intended place in the knee joint.

While existing devices, systems, and methods have attempted to address these issues, they have not been satisfactory in all respects. Accordingly, there is a need for the improved devices, systems, and methods in accordance with the present disclosure.

SUMMARY

In one embodiment, a floating meniscus prosthetic device is disclosed having anti-migration features.

In another embodiment, a prosthetic device for replacing a damaged meniscus is disclosed. The prosthetic device comprises a central portion having an upper surface for engagement with a portion of a femur and an opposing lower surface for engagement with a portion of a tibia. The central portion comprises a resilient material. The prosthetic device also includes an outer portion surrounding the central portion and having an increased thickness relative to the central portion. The outer portion comprises the resilient material and is tensioned with at least one reinforcing fiber embedded in the resilient material. The outer portion includes a retention structure sized and shaped to prevent posterior migration of the prosthetic device. In one aspect, the retention structure includes a posterior channel configured to engage a posterior remnant of the meniscus. In still a further aspect, the channel includes a posteriorly extending inferior plow blade configured to slide under at least a portion of the remnant of the meniscus. In still a further aspect, the retention structure includes an enlarged anterior flange configured to engage an anterior tibia and/or femoral edge adjacent the joint to inhibit posterior migration. In one feature, the anterior flange has a height that is at least 30 percent greater, and is some embodiments up to 100 percent greater, than the posterior height of the prosthetic device. In another aspect, the anterior flange includes an inferior extension that is greater than the superior extension. In an alternative form, the superior extension of the anterior flange is greater than the inferior extension. In yet a further form, the retention structure includes one or more fiber reinforced tethering extensions extending from the outer surface of the prosthetic device. In one aspect the tethering extensions are loops, while in another form the extensions are fiber reinforced tabs extending outwardly from the sidewall of the device. These tethering extensions can include fibers, bulk material or both. These loops, when including fibers, may anchor around the reinforcement fiber.

In another embodiment, a method is provided for replacing the function of a meniscus within a joint. The method of replacing the meniscus function within a joint includes removing a portion of a meniscus within the joint and leaving intact a meniscus remnant, then inserting a free floating meniscus replacement implant into the joint and engaging the meniscus replacement implant with the meniscus remnant such that the meniscus replacement implant is at least in part retained within the joint by the meniscus remnant. In a further aspect, the meniscus replacement implant includes a retention channel within the sidewall of the implant and the method of engaging the meniscus replacement implant with the meniscus remnant includes aligning the retention channel with the meniscus remnant. In still a further feature, the retention channel is a retention channel formed in a posterior portion of a knee meniscus replacement implant and the engaging includes aligning the retention channel with a posterior portion of the meniscus remnant. In yet a further aspect, the engaging includes suturing a portion of the meniscus replacement implant to a portion of the meniscus remnant or to tissue of the joint capsule adjacent the joint.

In still a further feature of the present disclosure, a method of implanting a prosthetic meniscus device is disclosed that permits in-vivo trialing of the implant that, if on trialing confirmed to be the correct sized implant, will remain in situ as final implantation. More specifically, the method includes providing an implant with one or more removable radiopaque markers. In one aspect, the radiopaque markers extend around at least a portion of the outer wall perimeter of the prosthetic meniscus device. In still a further feature, the radiopaque markers extend completely around the device. The method includes positioning the device, including the radiopaque markers, in the joint and then moving the joint through a range of motion while monitoring the movement of the radiopaque markers via radiographic visualization. After it is determined that the prosthetic meniscus implant functions properly within the joint, the radiopaque markers are removed. In one aspect, the radiopaque markers include a retention assembly and the retention assembly is released in vivo and the radiopaque markers are removed from the device while the device is positioned in the joint. In one aspect, the radiopaque markers are thin sheets of material. In another form, the radiopaque markers include radiopaque filaments.

In yet a further aspect of the present disclosure, a prosthetic meniscus device is provided with a removable radiopaque marker assembly. In one aspect, the radiopaque marker assembly is provisionally retained on the outer side walls of the device. In another form, the radiopaque marker assembly includes an external retention assembly configured for in vivo release such that the retention assembly can be released while the device is positioned within a joint.

BRIEF DESCRIPTION OF DRAWINGS

Other features and advantages of the present disclosure will become apparent in the following detailed description of embodiments of the disclosure with reference to the accompanying of drawings, of which:

FIGS. 22-23 illustrate a pre-formed core component for a left medial meniscus replacement device.

FIG. 24 is a diagrammatic cross-sectional view of an implant including tethering loops.

DETAILED DESCRIPTION

Figure 1A:
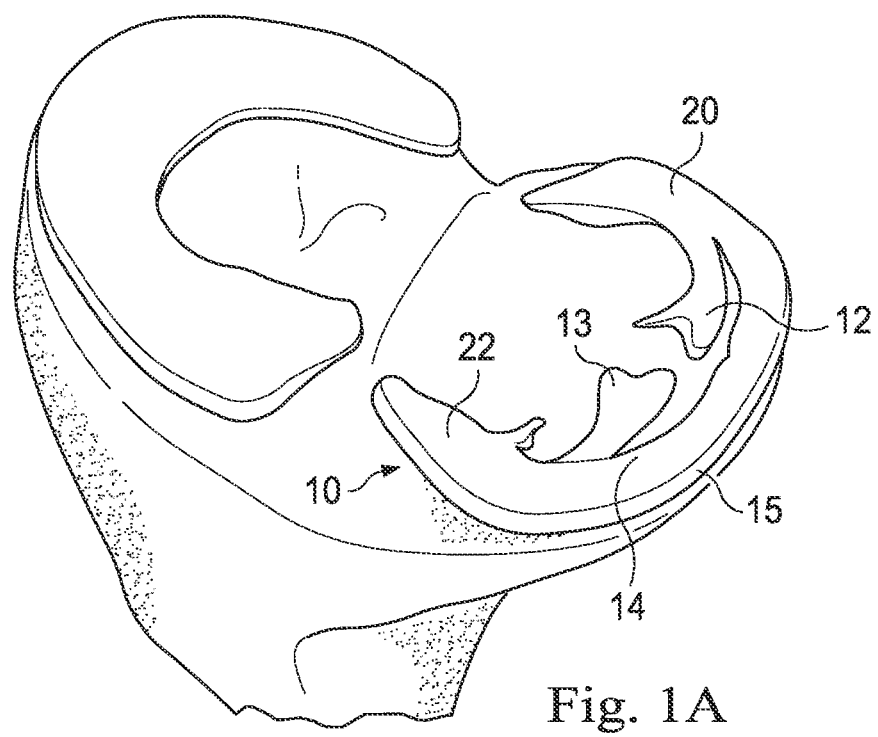
FIGS. 1A and 1B are diagrammatic perspective views of a right knee joint.

For the purposes of promoting an understanding of the principles of the present disclosure, reference will now be made to the embodiments illustrated in the drawings, and specific language will be used to describe the illustrated embodiments. It is nevertheless understood that no limitation of the scope of the disclosure is intended. Any and all alterations or modifications to the described devices, instruments, and/or methods, as well as any further application of the principles of the present disclosure that would be apparent to one skilled in the art are encompassed by the present disclosure even if not explicitly discussed herein. Further, it is fully contemplated that the features, components, and/or steps described with respect to one embodiment may be combined with the features, components, and/or steps described with respect to other embodiments of the present disclosure.

Figure 1B:
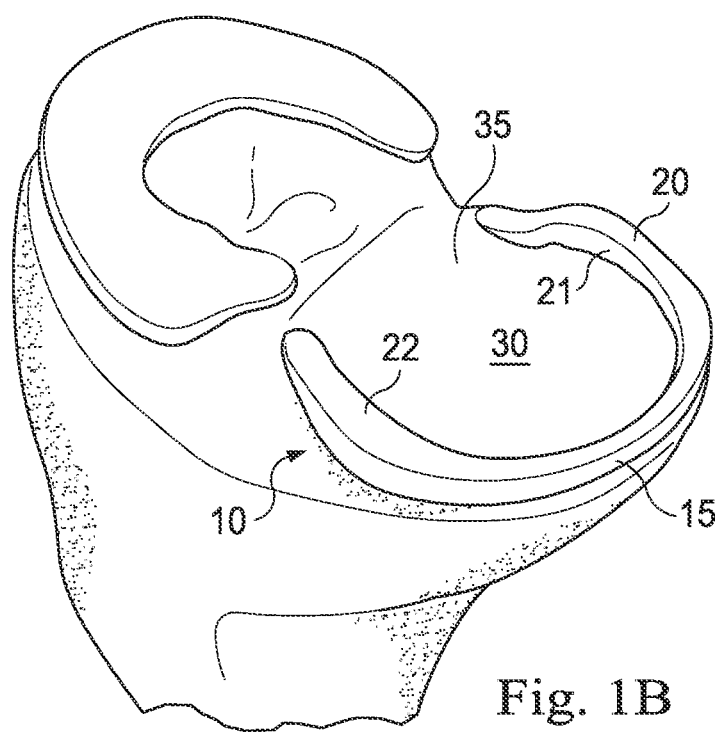
Figure 2:
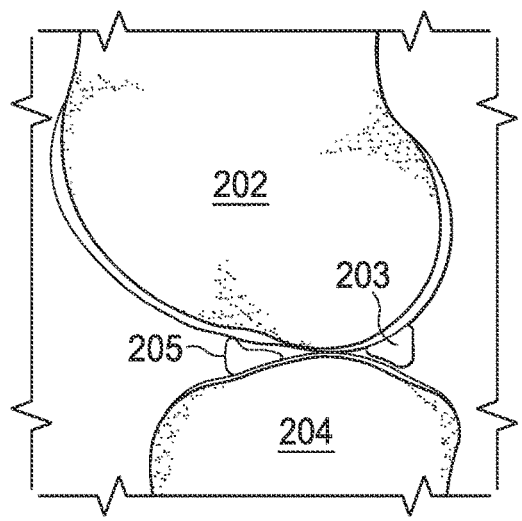
FIG. 2 is a diagrammatic side view of a right knee joint.

Referring now to FIG. 1A, there is shown a top view of a knee joint with an injured meniscus 10. The illustrated meniscus 10 has a tear between torn segments 12 and 13 extending from an undamaged remainder 14. The meniscus includes an outer rim 15 that is anchored to the bone along the posterior rim 20 and the anterior rim 22. Referring to FIG. 1B, the torn segments 12 and 13, along with the undamaged central meniscus 14 have been removed to expose the underlying tibia 35 and define an implantation area 30. The implantation area 30 is bounded by sidewall 21. FIG. 2 illustrates a side view of a knee joint between femur 202 and tibia 204. A partial meniscus having anterior portion 205 and posterior portion 203 shown extending between the adjacent bones.

Figure 3:
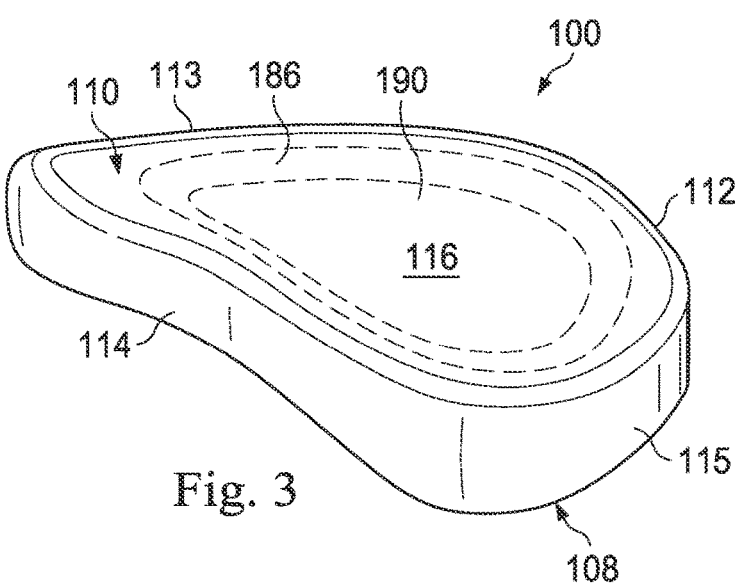
FIG. 3 is a diagrammatic perspective view of a prior art left medial prosthetic device.
Figure 4:
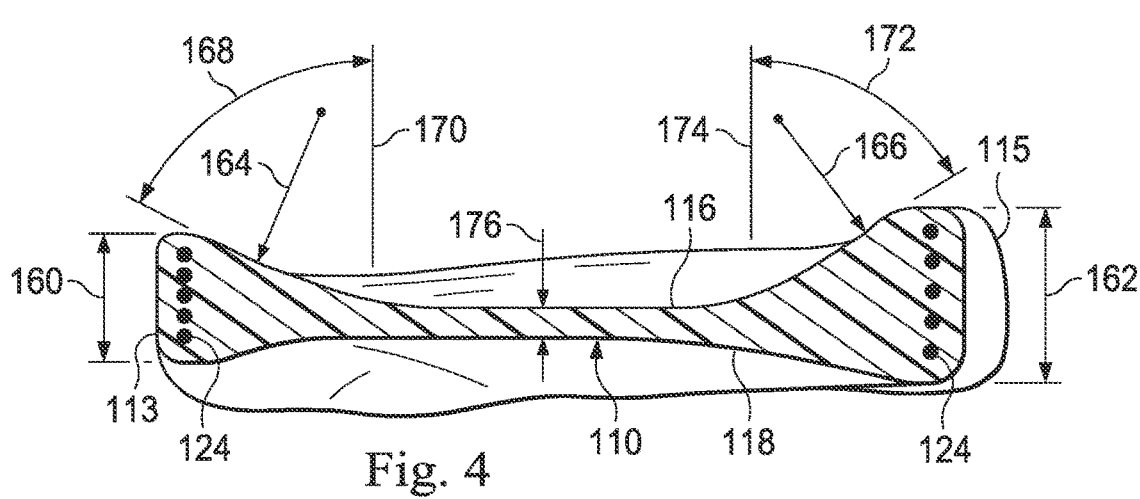
FIG. 4 is a diagrammatic cross-sectional view of the prosthetic device of FIG. 3.
Figure 5A:
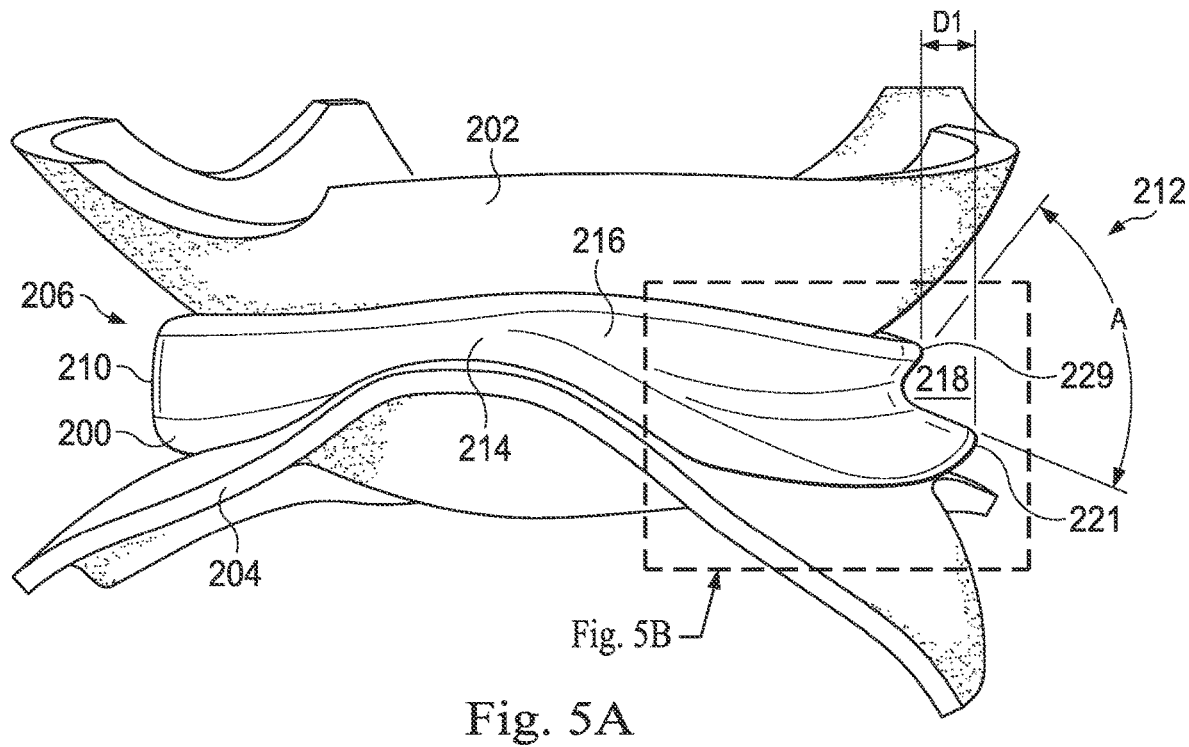
FIGS. 5A-6B are diagrammatic illustrations of a prosthetic device of a first embodiment positioned in the knee joint.
Figure 5B:
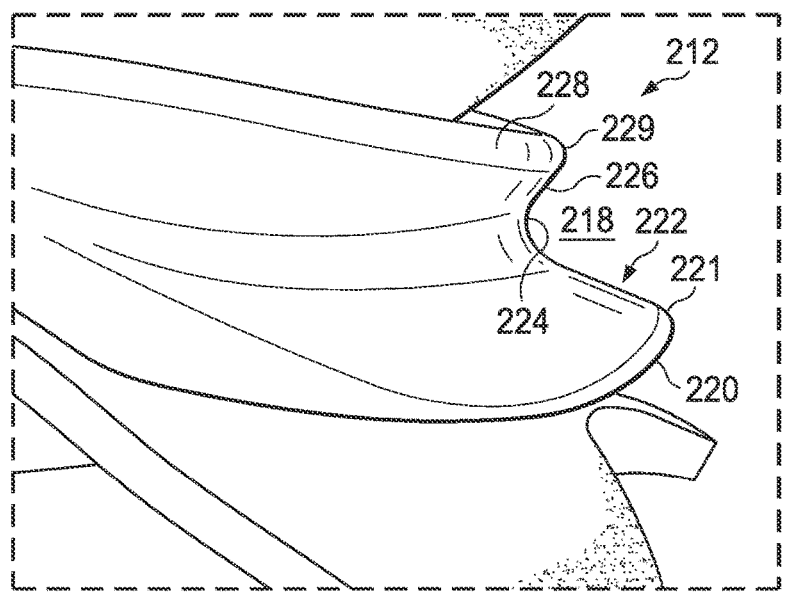

Referring now to FIGS. 3 and 4 shown therein is a prosthetic device 100 according to a prior design set forth in U.S. Pat. No. 8,361,147, which is hereby incorporated by reference in its entirety. Generally, the prosthetic device 100 is for the replacement of a meniscus that has been partially or totally meniscectomized before, damaged, ruptured, disintegrated, diseased, or is otherwise in need of replacement. For illustrative purposes, the prosthetic device 100 will be described in conjunction with a left knee, medial meniscus replacement. However, corresponding embodiments are utilized for replacement of any of the other menisci, such as the right knee medial meniscus, left knee lateral meniscus, and/or right knee lateral meniscus. In that regard, the size, shape, thickness, material properties, and/or other properties of the prosthetic device may be configured for each particular application.

The prosthetic meniscus 100 comprises an outer body portion 108 and a central body portion 110. Generally, the outer body portion 108 has an increased thickness and height relative to the central body portion 110. In some instances the outer body portion 108 has a thickness between 5 mm and 15 mm. In some instances, the central body portion 110 has a thickness between 0.5 mm and 5 mm. In one particular embodiment, the outer body portion 108 has a maximum thickness of approximately 10 mm and the central body portion 110 has a maximum thickness of approximately 2 mm. The height or thickness of the outer body portion 108 varies around the perimeter of the prosthetic device 100 in some instances. In that regard, the variations in the height or thickness of the outer body portion 108 are selected to match the anatomical features of the patient in some embodiments. Similarly, the height or thickness of the central body portion 110 varies across the prosthetic device 100 in some embodiments. Again, the variations in the height or thickness of the central body portion 110 are selected to match the anatomical features of the patient in some embodiments. In some embodiments, the prosthetic device 100 is inserted in an insertion configuration and then loaded, stretched, moved, and/or otherwise transferred to an implantation configuration. In some embodiments the transformation between the insertion configuration and the implantation configuration is facilitated through the loading of the prosthetic device 100.

In such embodiments, the variations in height or thickness of the outer and central body portions 108, 110 are selected to accommodate the deformation or transformation between the insertion configuration and the implantation configuration.

In the illustrated embodiment, the prosthetic device 100 is configured for use without a fixation member or fixation device that would penetrate an adjacent bone and/or soft tissue to keep the prosthetic device in place. Rather, the prosthetic device 100 is configured to "float" within the knee joint without being secured by such bone and/or soft tissue-penetrating fixation devices or otherwise rigidly fixed to the femur or tibia and/or surrounding soft tissue. To that end, the outer body portion 108 of the prosthetic device 100 is shaped and sized to prevent unwanted expulsion of the prosthetic device 100 from the knee joint. The prosthetic device 100 is implanted into a patient without causing permanent damage to the patient's tibia or other bone and/or soft tissue structure (s) engaged by the prosthetic device in some embodiments. In some instances the prosthetic device 100 is implanted to alleviate the patient's knee problems while avoiding permanent destruction of the patient's anatomy, such as cutting or reaming a large opening in the tibia. In such instances, the prosthetic device 100 may be subsequently removed and replaced with another prosthetic device or treatment without adversely affecting the subsequent treatment.

To this end, the outer body portion 108 of the prosthetic device 100 includes a first portion 112 and a second portion or bridge 114. In some embodiments, the first portion 112 substantially matches the shape of a natural meniscus. In some embodiments, the outer body portion 108 has a semi-ellipsoidal shape. Accordingly, the first portion 112 extends around a majority of the outer body portion 108. The bridge 114 connects the two ends of the first portion 112. Thus, where the prosthetic device is configured for use as a medial meniscus device, the bridge 114 extends along the lateral side of the device. Where the prosthetic device 100 is configured for use as a lateral meniscus device, the bridge 114 extends along the medial side of the device. Accordingly, the outer body portion 108—comprised of the first portion 112 and the bridge 114 and having an increased thickness relative to the central body portion 110—completely surrounds the central body portion 110 and serves to limit movement of the prosthetic device 100 after implantation. That is, the increased height of the outer body portion 108 along with the contact pressure on the prosthetic device 100 from being positioned between the femur and the tibia prevents the prosthetic device from moving outside of the desired range of positions within the knee joint.

The height or thickness of the bridge component 114 is based on the size of the femur notch and the distance to the cruciate ligaments in some embodiments. In some embodiments, the bridge 114 has a maximum height or thickness that is between ¼ and ¾ the maximum height or thickness of the first portion 112 of the outer body portion 108. In some embodiments, the size and shape of the bridge 114 is selected to achieve an optimal pressure distribution on the tibial plateau in order to mimic the pressure distribution of a healthy natural meniscus. The bridge 114 and, more generally, the outer body portion 108 are geometrically characterized by anterior, posterior, lateral-anterior, mid-lateral and lateral-posterior angles and heights as well as sagittal and coronal radii of curvature. Further, the outer body portion 108 and the central body portion 110 are shaped and sized such that the prosthetic device 100 is self-centering. That is, the shape and size of the prosthetic device 100 itself encourages the prosthetic device 100 to position or align itself with a desired orientation within the knee joint. Accordingly, as the prosthetic device 100 moves through a range of positions within the knee joint it naturally returns to the desired orientation due to the shape and size of the outer and central body portion 108, 110. In some embodiments, the outer body portion and, more specifically, the bridge 114 acts as a physical barrier limiting the movement of the prosthetic device caused by joint reaction forces. The self-centering or self-aligning mechanism combined with the prosthetic device's ability to move within the knee joint results in improved location of the prosthetic device 100 during typical gait cycles (e.g., flexion-extension angles of 0° to 120° or "heel-strike" to "toe-off"). The result is that the prosthetic device 100 exhibits a load pressure distribution similar to that of a natural meniscus.

The central body portion 110 defines an upper surface 116 and a lower surface 118. The upper and lower surfaces 116, 118 are both loaded surfaces. In particular, the upper and lower surfaces 116, 118 are configured to movingly engage with the femur and tibia, respectively. In that regard, the prosthetic device 100 can translate and rotate with respect to the femur and/or tibia within a range. In some instances, translation is possible in both the anterior-posterior and medial-lateral directions. In some embodiments, the upper surface 116 includes both a vertical and horizontal surface. To that end, in some embodiments the upper surface 116 comprises a concave surface that defines the vertical and horizontal surfaces. The thickness of the central body portion 110 between the upper surface 116 and the lower surface 118 supports stress distribution capability of the component, while the increased height of the upper surface 116 as it extends outwardly towards the outer body portion 108 defines the horizontal surface of the component. Similarly, in some embodiments the lower surface 118 includes both vertical and horizontal components. In particular, in some embodiments the lower surface 118 comprises a convex surface. In some embodiments, the upper surface 116 and/or the lower surface 118 are shaped such that the prosthetic device 100 is biased towards a neutral position in the knee. For example, the arcuate profiles of the upper surface 116 and/or the lower surface 118 are shaped such that the interaction between the surfaces and the cartilage encourages the implant to a particular orientation relative to the surfaces. This allows the prosthetic device 100 to be self-centering or self-aligning in some embodiments as discussed above with respect to the outer body portion 108.

Referring to FIG. 4, shown therein is a diagrammatic cross-sectional view of the prosthetic device 100 taken along an anterior to posterior section line between anterior end 113 and posterior end 115. The central body 110 is reinforced by pre-tensioned fibers 124 wound around the core to inhibit outward deformation while allowing inward flexibility. As shown, the anterior portion 113 of the outer body portion 108 has an anterior height or thickness 160. In that regard, the anterior height or thickness 160 of the anterior end 113 is between about 4 mm and immediately adjacent bridge structure 114 could be as great as about 15 mm and, in some instances, is between about 5.7 mm and about 9.3 mm. In the present embodiment, the anterior height or thickness 160 of the anterior end 113 is approximately 7.8 mm. In a smaller embodiment, the anterior height or thickness 160 is approximately 5.7 mm. In a larger embodiment, the anterior height or thickness 160 is approximately 9.3 mm. The posterior height or thickness 162 of the posterior end 114 is between about 4 mm and immediately adjacent the bridge structure 114 could be as great as about 20 mm and, in some instances, is between about 7.7 mm and about 12.7 mm. In the present embodiment, the posterior height or thickness 162 of the posterior end 115 is approximately 9.0 mm. In a smaller embodiment, the posterior height or thickness 162 is approximately 7.7 mm. In a larger embodiment, the posterior height or thickness 162 is approximately 12.7 mm.

The anterior portion of the upper surface of the anterior portion 113 has an anterior radius of curvature 164. In that regard, the anterior radius of curvature 164 is between about 10 mm and about 100 mm and, in some instances, is between about 23.0 mm and about 33.1 mm. In the present embodiment, the radius of curvature 164 is approximately 72 mm. In another embodiment, the radius of curvature 164 is approximately 28 mm. In a smaller embodiment, the radius of curvature 164 is approximately 23 mm. In a larger embodiment, the radius of curvature 164 is approximately 33.1 mm. The posterior portion of the upper surface of the posterior portion 115 has a posterior radius of curvature 166. In that regard, the posterior radius of curvature 166 is between about 5 mm and about 70 mm and, in some instances, is between about 15.2 mm and about 24.2 mm. In the present embodiment, the radius of curvature 166 is approximately 30 mm. In a smaller embodiment, the radius of curvature 166 is approximately 15.2 mm. In a larger embodiment, the radius of curvature 166 is approximately 24.2 mm.

Further, the anterior portion 113 of the upper surface generally extends at an anterior angle 168 with respect to an axis 170 extending substantially perpendicular to a plane generally defined by the prosthetic device 100, as shown. The anterior angle 168 is between about 45 degrees and about 75 degrees and, in some instances, is between about 62 degrees and about 68 degrees. In the present embodiment, the angle 168 is approximately 65 degrees. In a smaller embodiment, the angle 168 is approximately 62 degrees. In a larger embodiment, the angle is approximately 68 degrees. The posterior portion 115 of the upper surface generally extends at an posterior angle 172 with respect to an axis 174 extending substantially perpendicular to a plane generally defined by the prosthetic device 100, as shown. The posterior angle 172 is between about 35 degrees and about 70 degrees and, in some instances, is between about 55 degrees and about 61 degrees. In the present embodiment, the angle 172 is approximately 58 degrees. In a smaller embodiment, the angle 172 is approximately 50 degrees. In a larger embodiment, the angle 172 is approximately 65 degrees.

The central body portion 110 has a height or thickness 176 between the upper articulation surface 116 and the lower articulation surface 118. In some embodiments, the height or thickness 176 is the minimal thickness of the central body portion 110 and, in more specific embodiments, the minimal thickness of the entire prosthetic device 100. To that end, the height or thickness 176 is between about 1 mm and about 3 mm and, in some instances, is between about 1.2 mm and about 2.1 mm. In the present embodiment, the height or thickness 176 is approximately 1.5 mm. In a smaller embodiment, the height or thickness 176 is approximately 1.2 mm. In a larger embodiment, the height or thickness 176 is approximately 2.1 mm.

A variety of materials are suitable for use in making the prosthetic devices of the present disclosure. Medical grade polyurethane based materials especially suitable for use in the embodiments described include, but are not limited to, isolated or in combination, the following:

Bionate®, manufactured by DSM, a polycarbonate-urethane is among the most extensively tested biomaterials ever developed. Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability. Bionate® polycarbonate-urethane is a thermoplastic elastomer formed as the reaction product of a hydroxyl terminated polycarbonate, an aromatic diisocyanate, and a low molecular weight glycol used as a chain extender. The results of extensive testing encompassing Histology, Carcinogenicity, Biostability, and Tripartite Biocompatibility Guidance for Medical Devices verifies the cost effective material's biocompatibility.

Another group of suitable materials are copolymers of silicone with polyurethanes as exemplified by PurSil™, a Silicone Polyether Urethane and CarboSil™, a Silicone Polycarbonate Urethane. Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted. In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have an excellent flex life, tensile strength exceeding 5000 psi, and ultimate elongations greater than 700 percent. These materials are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, in polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo. DSM synthesized silicone-polyurethane copolymers by combining two previously reported methods: copolymerization of silicone (PSX) together with organic (non-silicone) soft segments into the polymer backbone, and the use of surface-modifying end groups to terminate the copolymer chains.

Other applicable materials include PurSil™ silicone-polyether-urethane and CarboSil™ silicone-polycarbonate-urethane which are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminated polycarbonate (CarboSil). The hard segment consists of an aromatic diisocyanate, MDI, with low molecular weight glycol chain extender. The copolymer chains are then terminated with silicone (or other) Surface-Modifying End Groups. Aliphatic (AL) versions of these materials, with a hard segment synthesized from an aliphatic diisocyanate, are also available.

Many of these silicone urethanes demonstrate desirable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Properties). These properties make these materials very attractive as high-performance substitutes for conventional cross-linked silicone rubber. In both the PTMO and PC families, some polymers have tensile strengths three to five times higher than conventional silicone biomaterials.

Further examples of suitable materials include Surface Modifying End Groups (SMEs) which are surface-active oligomers covalently bonded to the base polymer during synthesis. SMEs—which include silicone (S), sulfonate (SO), fluorocarbon (F), polyethylene oxide (P), and hydrocarbon (H) groups—control surface chemistry without compromising the bulk properties of the polymer. The result is that key surface properties, such as thromboresistance, biostability, and abrasion resistance, are permanently enhanced without additional post-fabrication treatments or topical coatings. This technology is applied to a wide range of DSM's polymers.

SMEs provide a series of base polymers that can achieve a desired surface chemistry without the use of additives. Polyurethanes prepared according to DSM's development process couple endgroups to the backbone polymer during synthesis via a terminal isocyanate group, not a hard segment. The added mobility of endgroups relative to the backbone facilitates the formation of uniform overlayers by the surface-active end blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymers amphipathic characteristics in which the hydrophobic versus hydrophilic balance may be easily controlled.

Other suitable materials, manufactured by CARDIOTECH CTE, include ChronoFlex® and Hydrothane™.

The ChronoFlex®, polycarbonate aromatic polyurethanes, family of medical-grade segmented biodurable polyurethane elastomers have been specifically developed by CardioTech International to overcome the in vivo formation of stress-induced microfissures.

HydroThane™, hydrophilic thermoplastic polyurethanes, is a family of super-absorbent, thermoplastic, polyurethane hydrogels ranging in water content from 5 to 25% by weight. HydroThane™ is offered as a clear resin in durometer hardness of 80A and 93 Shore A. The outstanding characteristic of this family of materials is the ability to rapidly absorb water, high tensile strength, and high elongation. The result is a polymer having some lubricious characteristics, as well as being inherently bacterial resistant due to their exceptionally high water content at the surface. HydroThane™ hydrophilic polyurethane resins are thermoplastic hydrogels, and can be extruded or molded by conventional means. Traditional hydrogels on the other hand are thermosets and difficult to process.

Additional suitable materials manufactured by THERMEDICS include Tecothante® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane). Tecothane® is a family of aromatic, polyether-based TPU's available over a wide range of durometers, colors, and radiopacifiers. One can expect Tecothane resins to exhibit improved solvent resistance and biostability when compared with Tecoflex resins of equal durometers. Carbothane® is a family of aliphatic, polycarbonate-based TPU's available over a wide range of durometers, colors and radiopacifiers. This type of TPU has been reported to exhibit excellent oxidative stability, a property which may equate to excellent long-term biostability. This family, like Tecoflex, is easy to process and does not yellow upon aging. Tecophilic® is a family of aliphatic, polyether-based TPU's which have been specially formulated to absorb equilibrium water contents of up to 150% of the weight of dry resin.

Additional materials of interest include Tecogel, a new member to the Tecophilic family, a hydrogel that can be formulated to absorb equilibrium water contents between 500% to 2000% of the weight of dry resin, and Tecoplast®, a family of aromatic, polyether-based TPU's formulated to produce rugged injection molded components exhibiting high durometers and heat deflection temperatures.

Additional potentially suitable materials include four families of polyurethanes, named Elast-Eon™, which are available from AorTech Biomaterials.

Elast-Eon™ 1, a Polyhexamethylene oxide (PFMO), aromatic polyurethane, is an improvement on conventional polyurethane in that it has a reduced number of the susceptible chemical groups. Elast-Eon™2, a Siloxane based macrodiol, aromatic polyurethane, incorporates siloxane unto the soft segment. Elast-Eon™3, a Siloxane based macrodiol, modified hard segment, aromatic polyurethane, is a variation of Elast-Eon™2 with further enhanced flexibility due to incorporation of siloxane into the hard segment. Elast-Eon™ 4 is a modified aromatic hard segment polyurethane.

Bayer Corporation also produces candidate materials. Texin 4210 and Texin 4215 are thermoplastic polyurethane/polycarbonate blends for injection molding and extrusion. Texin 5250, 5286 and 5290 are aromatic polyether-based medical grade materials with Shore D hardness of approximately 50, 86, and 90 respectively for injection molding and extrusion.

Except as set forth specifically below, the following exemplar devices incorporate the features of the prior device described with respect to FIGS. 3 and 4 in terms of materials, function, outer surfaces and pre-tensioned core element as described herein and in more detail in U.S. Pat. No. 8,361,147, hereby incorporated by reference in its entirety.

Referring now to FIGS. 5A-6B, there is shown a meniscus replacement device 200 according to an embodiment of the present disclosure disposed in the joint 206 formed between femur 202 and tibia 204. The device 200 includes an anterior end portion 210 and an opposite posterior end portion 212. In the illustrated embodiment, the anterior end portion 210 along with the upper surfaces is formed similar to the implant of FIGS. 3 and 4 described above and, as discussed more fully below, the implant includes the fiber reinforcing and pre-tensioning members embedded within the implant to inhibit outward deformation. However, the posterior portion 212 has been modified to form a retention structure defining a posterior pocket 218. Beginning at transition area 216, the side wall 214 is divided into two fork portions 220 and 226. Fork portion 220 has a lower, inferior surface that extends the farthest posteriorly to define the leading edge 221 of portion 220. Fork portion 220 includes an upper, superior surface 222 extending toward the pocket bottom 224 that defines a plow or shovel blade shape. The pocket bottom 224 is a concave sidewall defining an inwardly extending recess that is defined in part by the inferior surface 222 and the superior surface 226. The inferior surface of 220 can either be concave, lifting off from the surface of the tibia plateau, or convex, following the curve of the tibia plateau. The superior 226 surface of the sidewall terminates at the upper surface 228 to define a leading tip 229 of the upper surface. The leading tip 229 extends more posteriorly than the upper surface 228 such that an overhang structure is created to better define a receiving pocket. In one aspect, the fork portion 220 has lower distal tip 221 extends a distance D1 of approximately 3 mm beyond the upper portion tip 229. In an alternative form, the upper and lower fork portions extend an equal distance posteriorly. In still a further form, the superior fork portion can extend farther posteriorly than the inferior fork portion. In the illustrated embodiment, the superior surface 222 extends at an angle A with respect to the superior surface of pocket 218. In one aspect, the angle A is less than 90 degrees, although angle A could be as high as 120 degrees. In still a further aspect, the angle A is approximately 75 degrees.

Figure 6A:
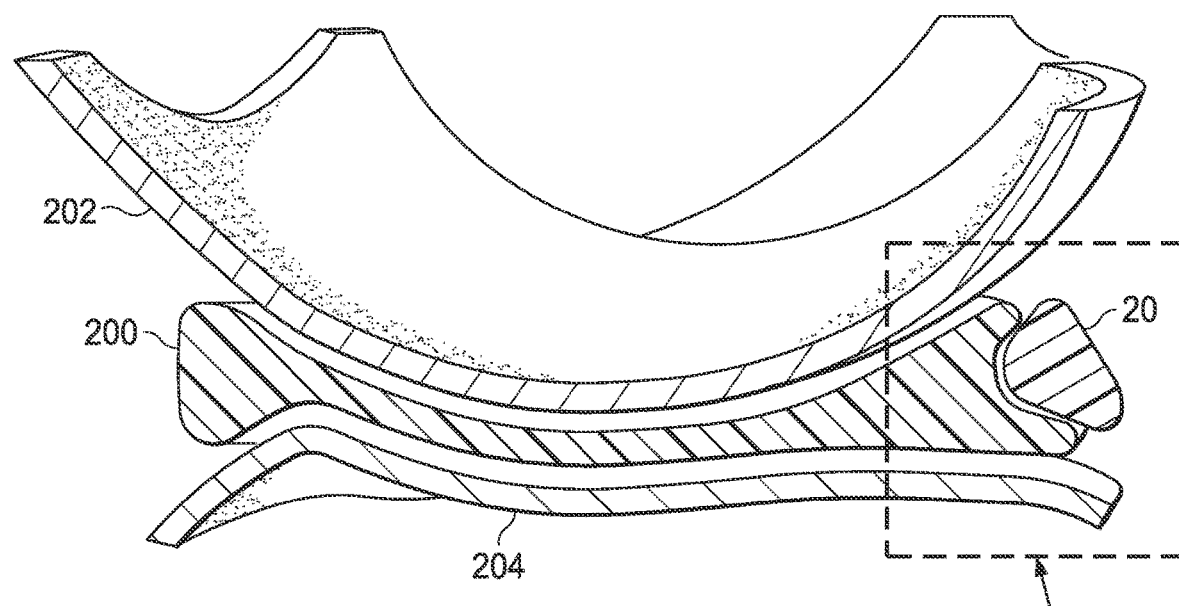
Figure 6B:
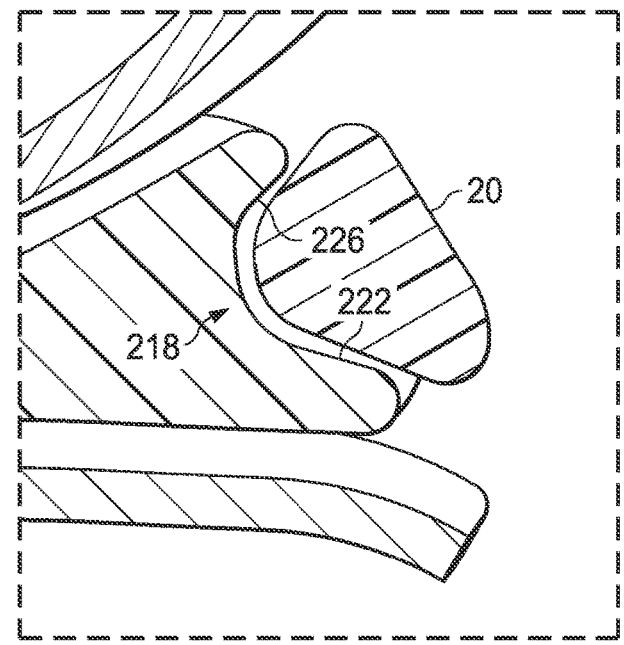
Figure 7A:
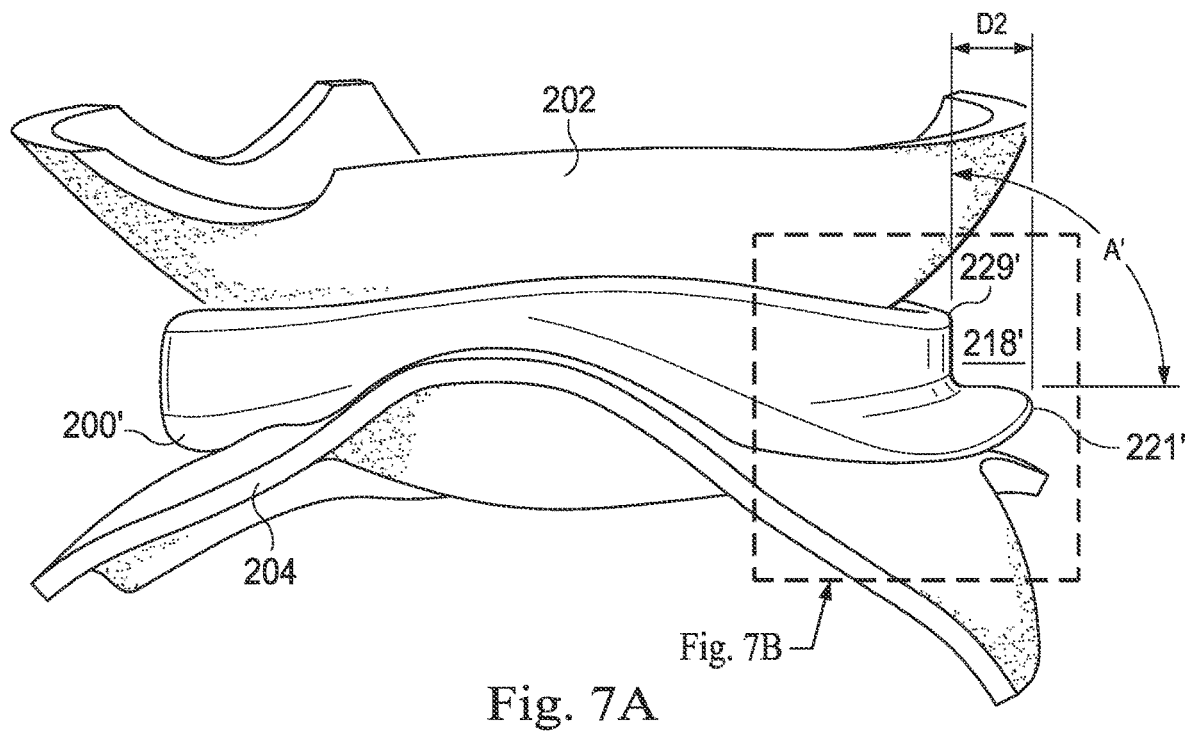
FIGS. 7A-8B are diagrammatic illustrations of a prosthetic device of a second embodiment positioned in the knee joint.
Figure 7B:
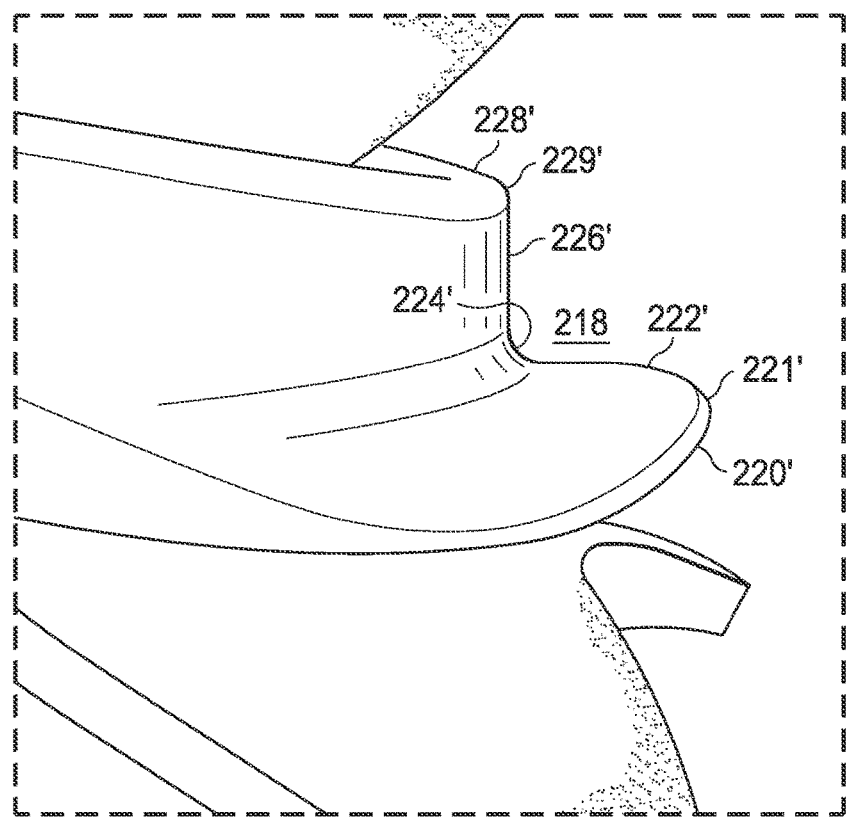

As illustrated in FIGS. 6A and 6B, the pocket 218 is configured to engage the posterior rim 20 of the remnants of the meniscus in the knee joint. The engagement of the posterior rim 20 within the socket 218 inhibits extreme movement of the meniscus device 200 posteriorly out of the knee joint. However, the device 200 is free to float within the space 30 as the knee joint moves through its range of motion. As the device 200 begins to move posteriorly, the leading fork 220 slides under the posterior rim 20 and the surface 222 guides the rim into the pocket 218.

Figure 8A:
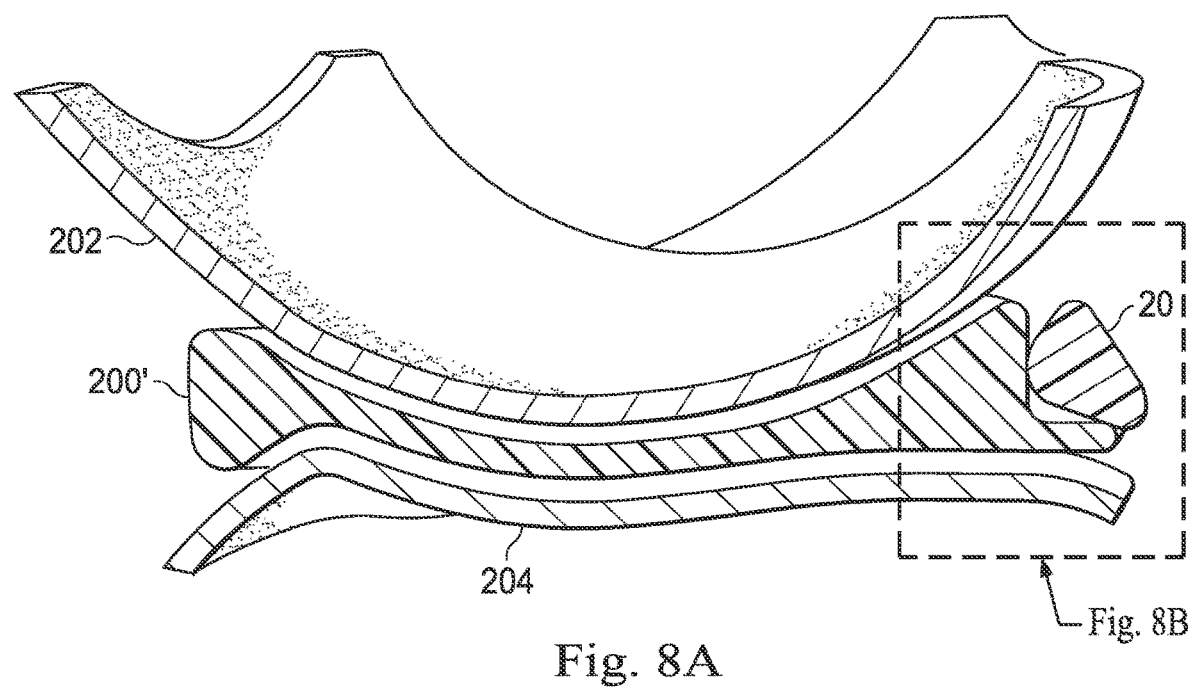
Figure 8B:
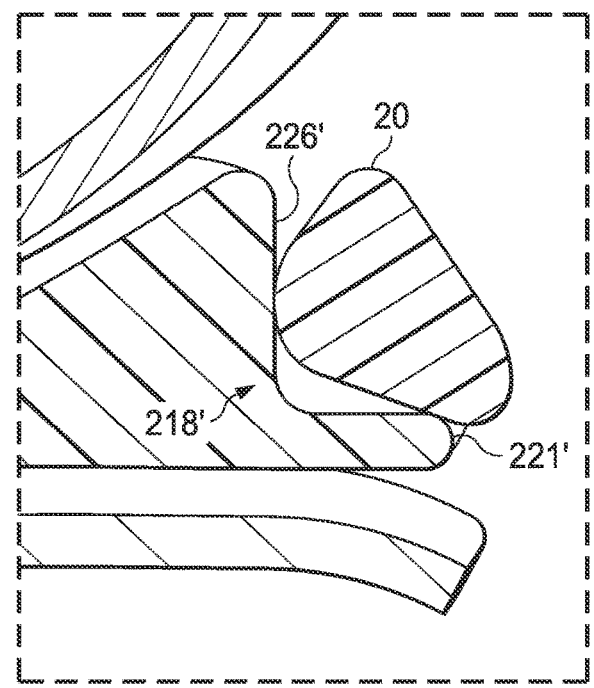
Figure 9:
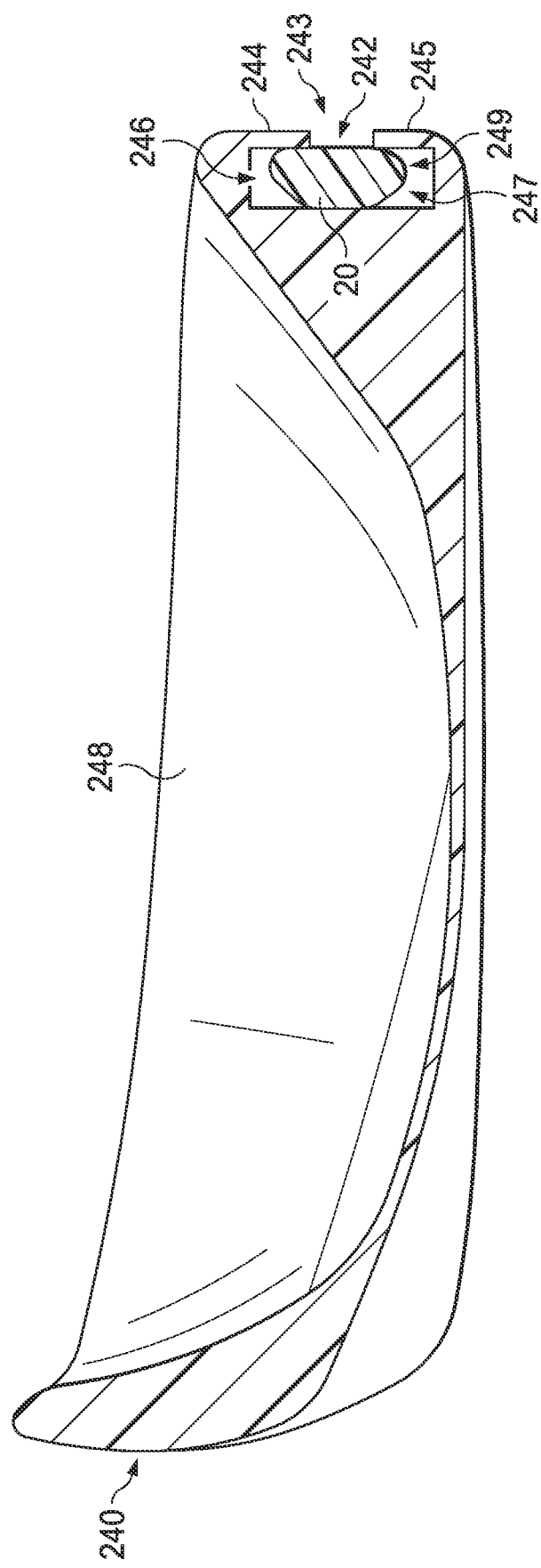
FIG. 9 is a diagrammatic cross-sectional illustration of a prosthetic device of a third embodiment.
Figure 10:
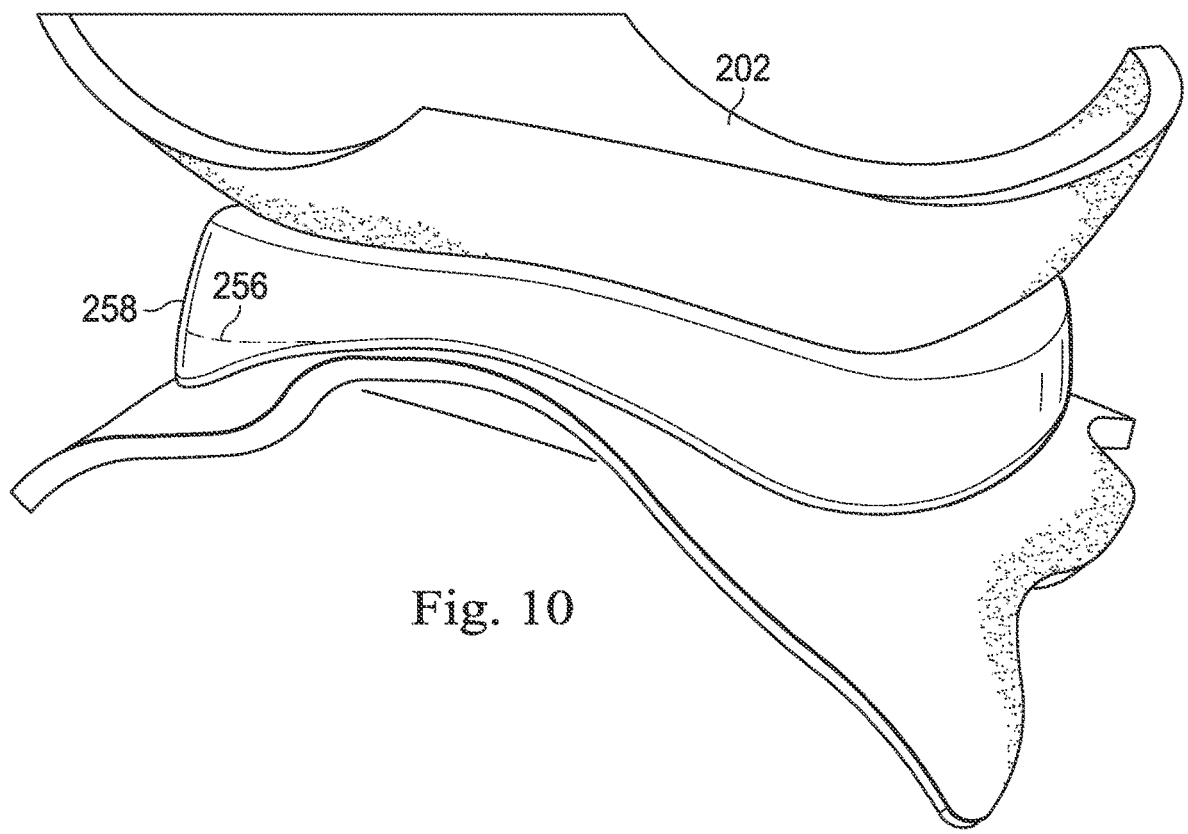
FIGS. 10-13B are diagrammatic illustrations of a prosthetic device of a fourth embodiment associated with the knee joint.

Referring now to FIGS. 7A-8B, there is shown still a further embodiment of a meniscus replacement device. The meniscus replacement device 200' has many of the same features as the device 200 of FIG. 6A, with the exception that the posterior pocket has been modified. More specifically, the distance between the lower posterior edge 221' and the upper posterior edge 229' has been increased to a distance D2 of approximately 5 mm such that wall 226' is substantially perpendicular to the longitudinal axis of the device to form a vertical wall. The resulting structure has an angle A' between side wall 226' and superior surface 222'. The angle A' can have a range similar to angle A described above. The resulting structure defines a plow or shovel blade shape having leading edge 221' following by angled surface 222'. As shown in FIGS. 8A and 8b, the plow blade feature extends under the posterior rim 20 and sidewall 226' engages the posterior rim 20 to inhibit further posterior migration of the implant 200' and/or "jumping" of implant 200 on top of the posterior meniscus remnants In still a further alternative illustrated in FIG. 9, the implant 240 is formed similar to the implant of FIGS. 3 and 4 with an upper surface 248 and a further alternative posterior retention structure 242. More specifically, the posterior sidewall defines an opening 243 defined between two flexible tabs 244 and 245. The opening 243 leads to an interior passage 249 having an upper channel 246 and a lower channel 247. As shown in FIG. 9, the posterior rim 20 may be inserted through opening 243 by movement of the flexible tabs 244 and 245. Once positioned in the channels 246 and 247, the posterior rim 20 can engage the implant to inhibit posterior movement as well as engaging the flexible tabs to inhibit anterior movement. Thus, the posterior retention structure 242 releasably joins the implant 240 to the posterior rim 20 so both will move together during loading cycles as the knee moves through its range of motion.

In a surgical procedure for replacement of a knee meniscus, the knee joint is prepared to provide an open area 30 as shown in FIG. 1B. While a complete rim 15 is shown in FIG. 1B, it is contemplated that the surgical preparation for implantation of the devices of FIGS. 5A-9 can include removal of the majority of rim 15 provided that posterior aspects 20 of the rim are retained. Once the joint space is prepared, the implant is inserted from an anterior opening into the joint space with the posterior retention structure oriented posteriorly. The implant is advanced until the posterior retention structure is positioned adjacent the posterior meniscus remnants 20. In one feature, the implant is advanced posteriorly until the blade or wedge 222 slides under the posterior meniscus remnants and they engage the posterior recess of the device. In alternative form, the implant is advanced posteriorly until the posterior remnants are engaged within the channel 243.

Figure 11:
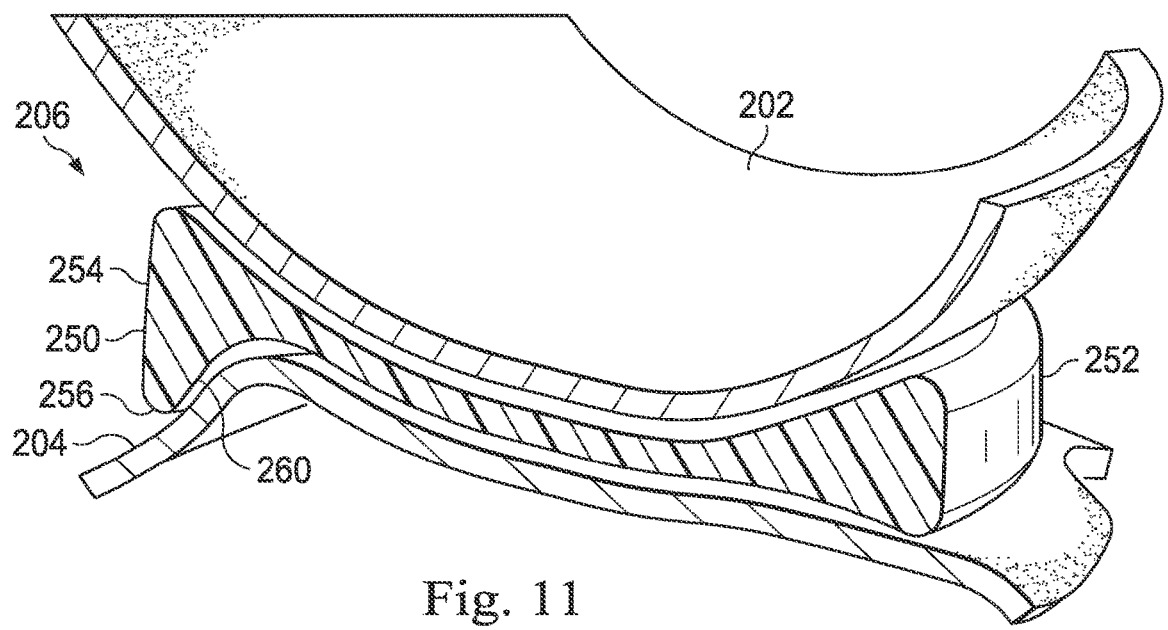
Figure 12:
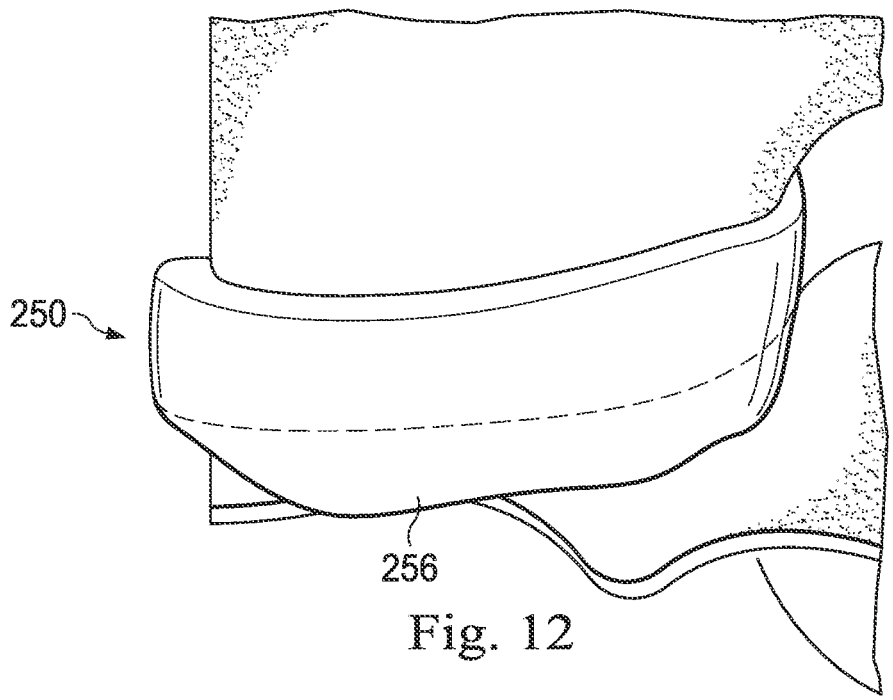
Figure 13A:
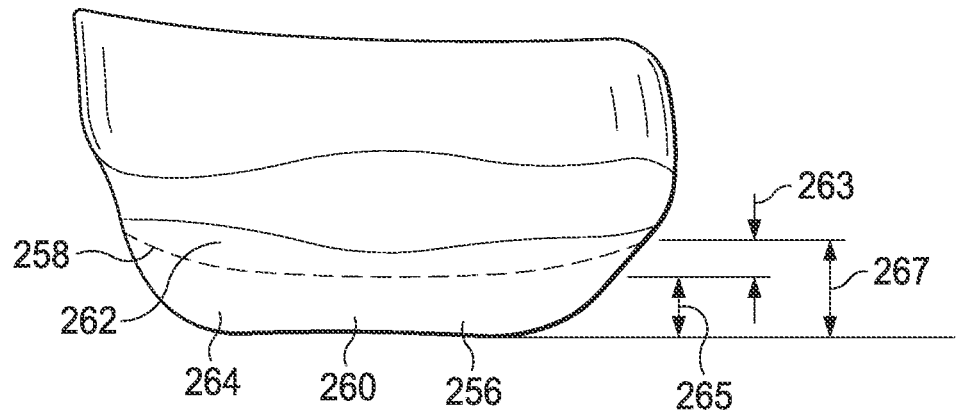
Figure 13B:
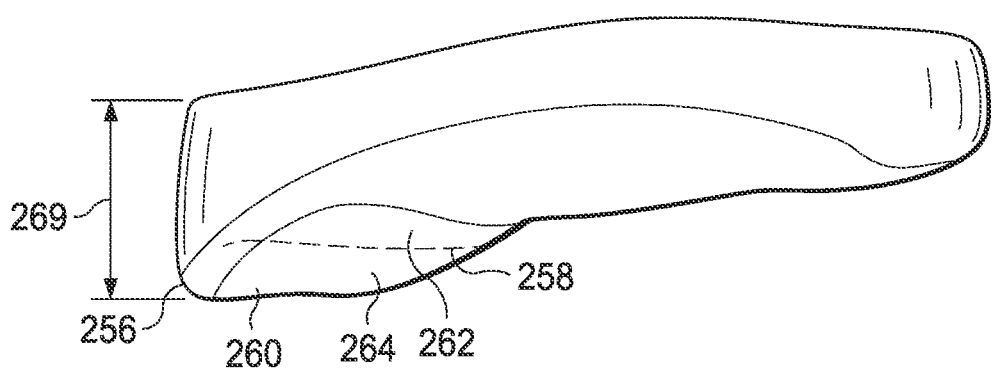
Figure 14:
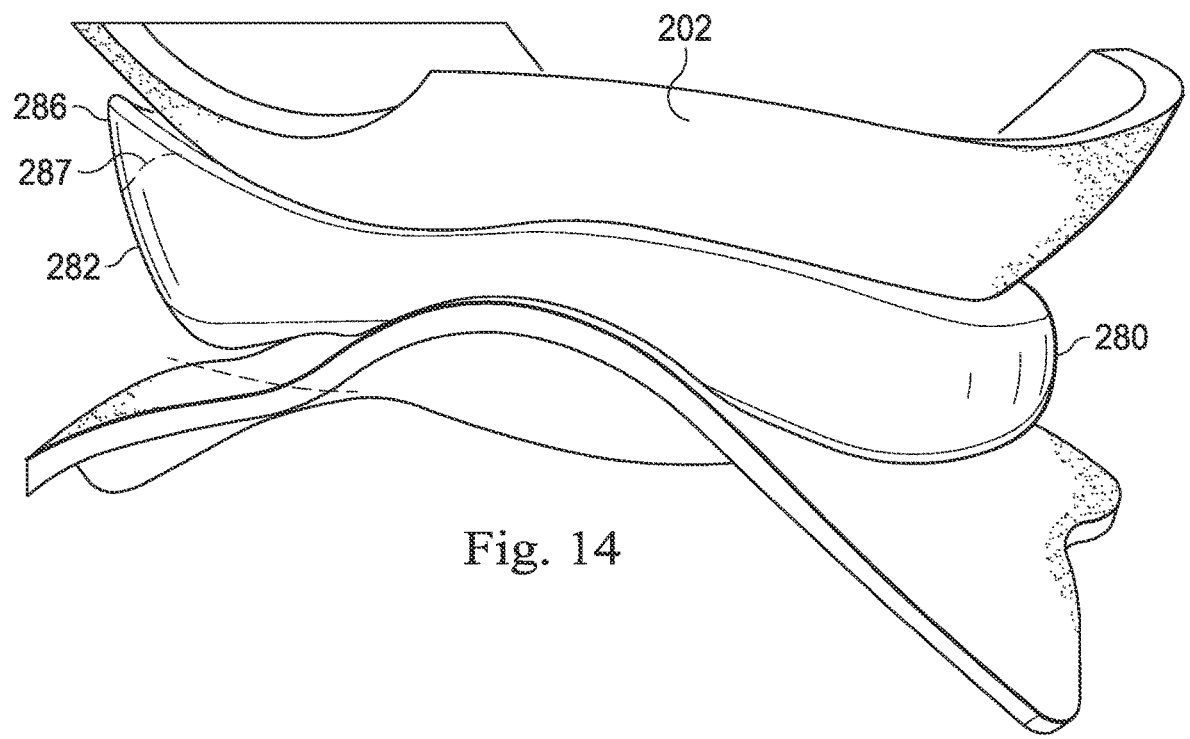
FIGS. 14-17B are diagrammatic illustrations of a prosthetic device of a further embodiment associated with the knee joint.
Figure 15:
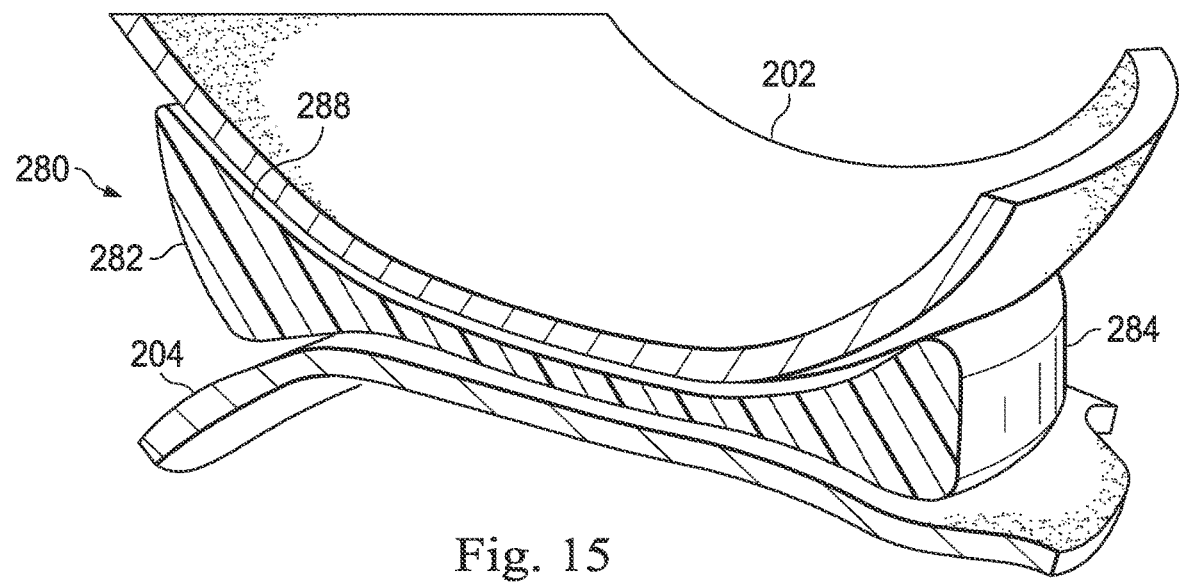
Figure 16:
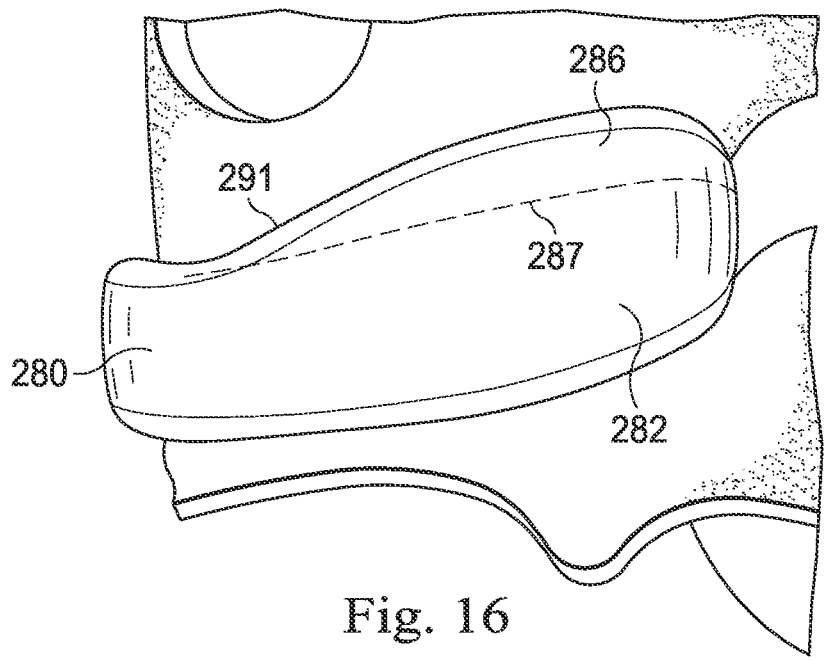
Figure 17A:
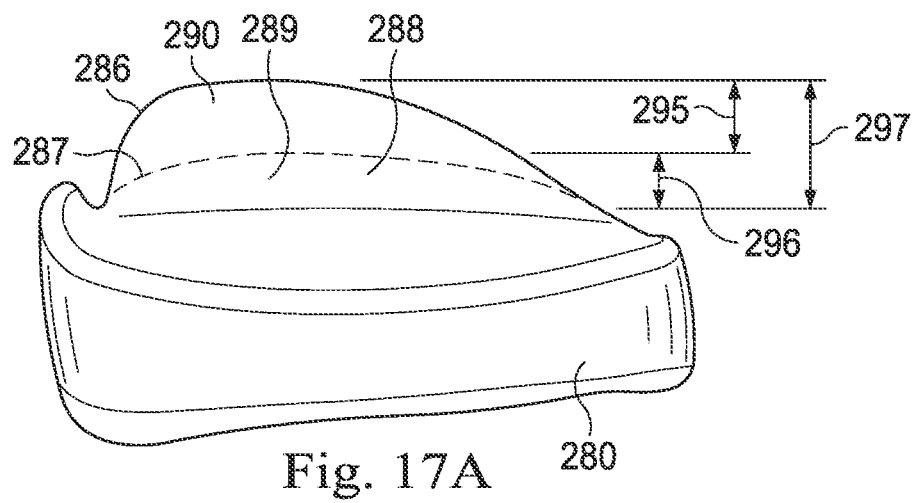
Figure 17B:
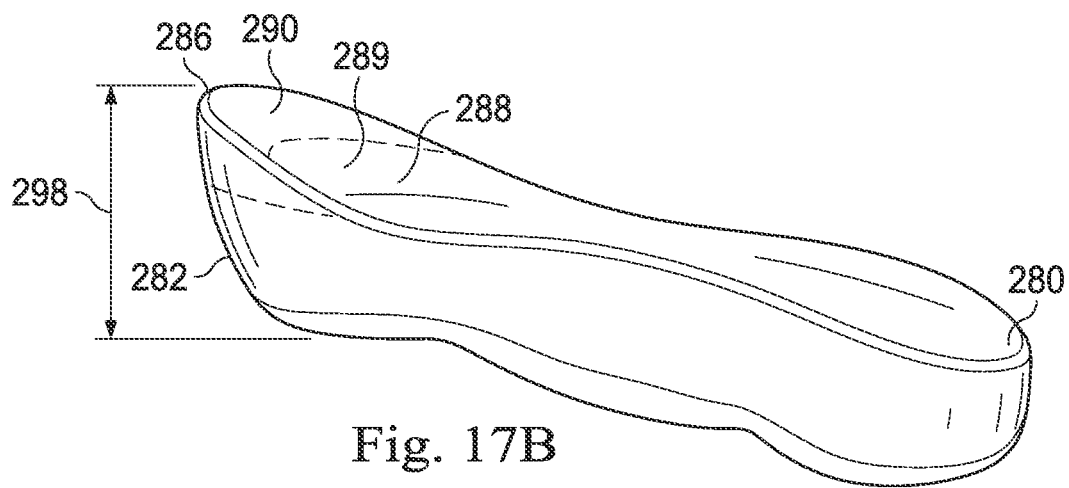

FIGS. 5A-9 illustrate a variety of posterior anti-migration features that are accomplished by posterior wall modifications while still permitting the implant to be free floating within the joint. In alternative configurations shown in FIGS. 10-21B, the implant is inhibited from extreme posterior migration by an anterior anti-migration structure defined along the anterior wall of the implant. More specifically referring to FIGS. 10-13B, there is shown an implant 250 disposed between the femur 202 and the tibia 204. FIG. 11 shows a cross sectional view taken along a plane extending from the anterior to posterior of the joint. The anterior portion 254 is disposed opposite the posterior portion 252. As explained above, the implant 250 has all of the features of the implant described with respect to FIGS. 3 and 4, including a similar posterior portion 252. However, the anterior portion 254 has been modified to define an anterior anti-migration structure. The dashed line 258 represents the lower, inferior edge of the implant disclosed in FIGS. 3 and 4. Thus, the inferior extension 256 defines the enhanced anterior anti-migration structure. The anti-migration structure 256 includes an inner superior surface 260 for loading against the tibia. The surface 260 includes an upper region 262 and a lower, extended region 264 that provides an extra length of wall to engage the tibia and prevent the implant from migrating posteriorly within the joint space. The upper region has a height 263 of approximately 1.5 mm, the lower region has a height 265 of approximately 2.5-4.5 mm giving the superior surface 260 an overall height of in the range of approximately 3-6 mm. With the addition of the lower extension, the implant has an anterior wall height 269 of 9-14 mm. As will be appreciated, for the illustrated embodiment, the posterior end wall has a height of approximately 9.0 mm. Thus, the anterior anti-migration structure 256 has a height that is about 50% greater than the height of the posterior end of the implant. In alternative form, the anterior wall height can be a much as twice as tall as the wall height of the posterior end of the implant.

Referring now to FIGS. 14-17B, there is shown a further embodiment of an implant 280 with an anterior anti-migration structure 286 according to another aspect of the present disclosure. The portions of the implant 280 extending between the anterior end 282 and posterior end 284 are substantially the same as described above with the exception of the anti-migration structure 286. The anti-migration structure 286 extends upwardly to define an inner superior surface 288 configured to engage a portion of femur 202. The dashed line 287 extending across said surface 288 illustrates the difference between the height of the superior surface 289 existing in the implant shown in FIGS. 3 and 4 and the anti-migration extension surface 290 extending substantially more superiorly. More specifically, the superior surface 289 has a height 296 of approximately 1.5 mm and the surface 290 has a height 295 of 2.5 to 4.5 mm, thereby defining a retention member surface 290 height 297 of 3-6 mm. The overall height 298 of the anterior anti-migration structure is 9-13 mm. As will be appreciated, for the illustrated embodiment, the posterior end wall as a height of approximately 9.0 mm. Thus, the anterior anti-migration structure 282 has a height that is about 50 percent greater than the height of the posterior end of the implant. In alternative form, the anterior wall height can be a much as twice as tall as the wall height of the posterior end of the implant. The superiorly extending anti-migration structure is configured to engage the femur to prevent unwanted posterior migration of the implant within the knee joint.

Figure 18:
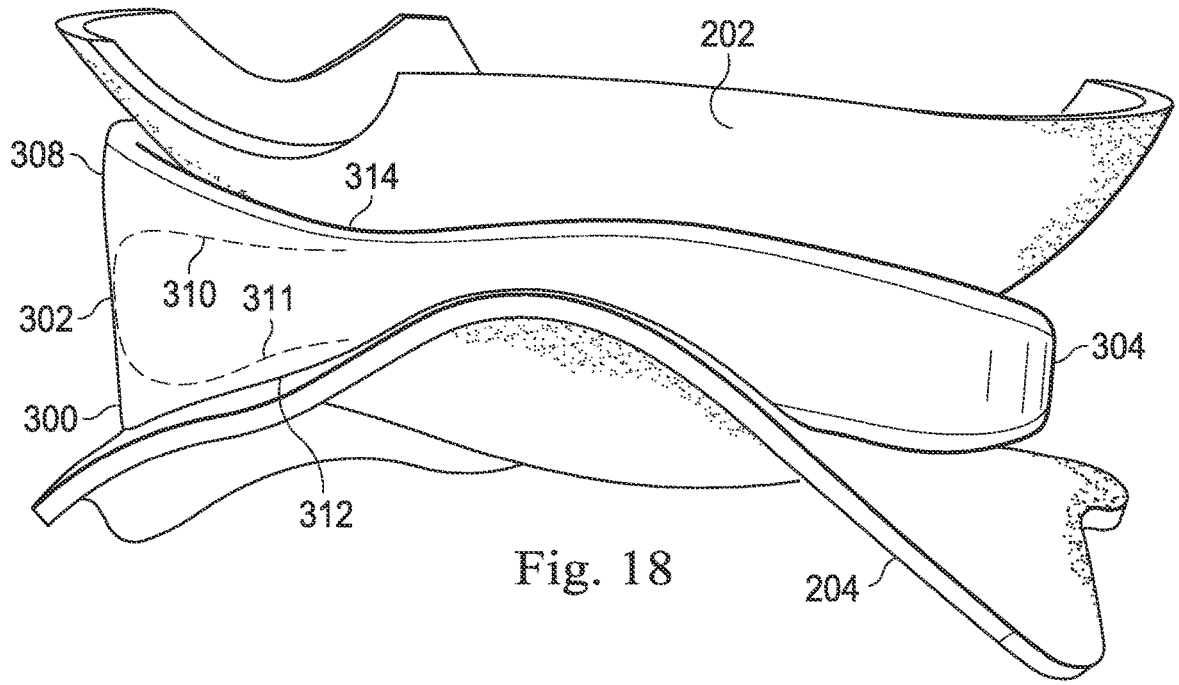
FIGS. 18-21B are diagrammatic illustrations of a prosthetic device of a still a further embodiment associated with the knee joint.
Figure 19:
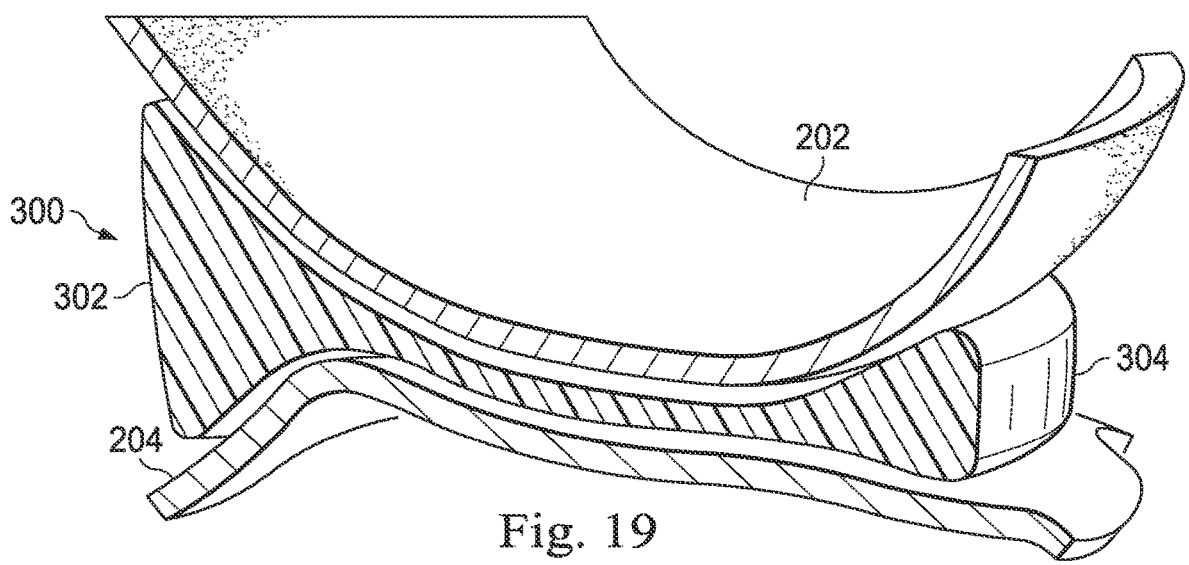
Figure 20:
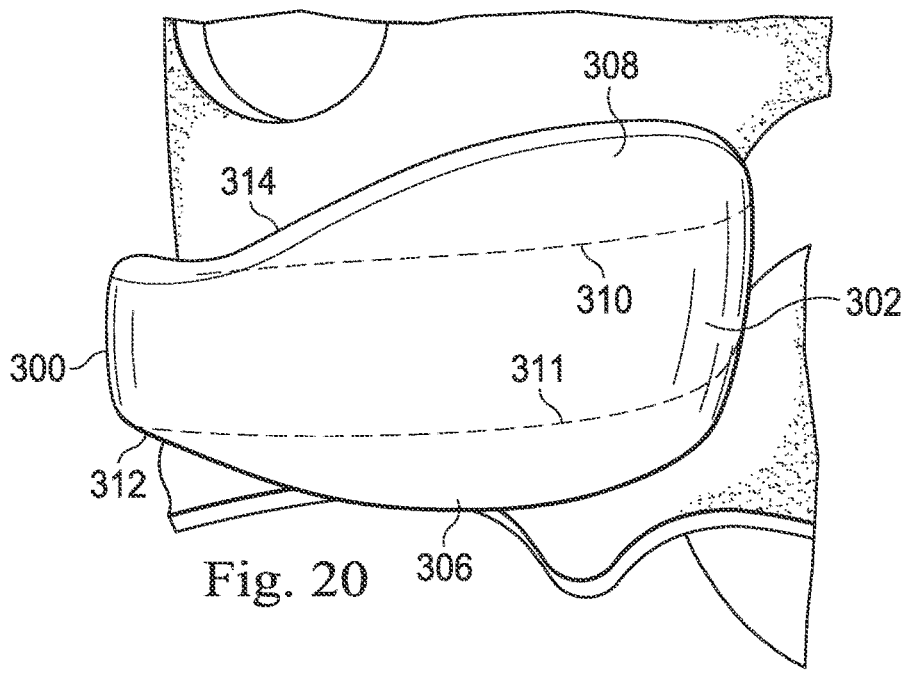

Referring now to FIGS. 18-21B, there is shown an implant 300 disposed between femur 202 and tibia 204. The portions of the implant 300 extending between the anterior end and posterior end 304 are substantially the same as described above with the exception of the anti-migration structure 302 formed on the anterior end. The anti-migration structure 302 includes a superior extension 308 and an inferior extension 306. As shown in FIG. 18, dashed lines 310 and 311 illustrate the height of a prior implant such as that shown in FIGS. 3 and 4. As illustrated, the upper or superior extension 308 begins at transition 314 on the upper edge of the sidewall and transitions to the maximum height at the anterior end. Similarly, the lower or interior extension 306 begins at transition 312 on the lower edge of the sidewall and transitions to the maximum height at the anterior end.

Figure 21A:
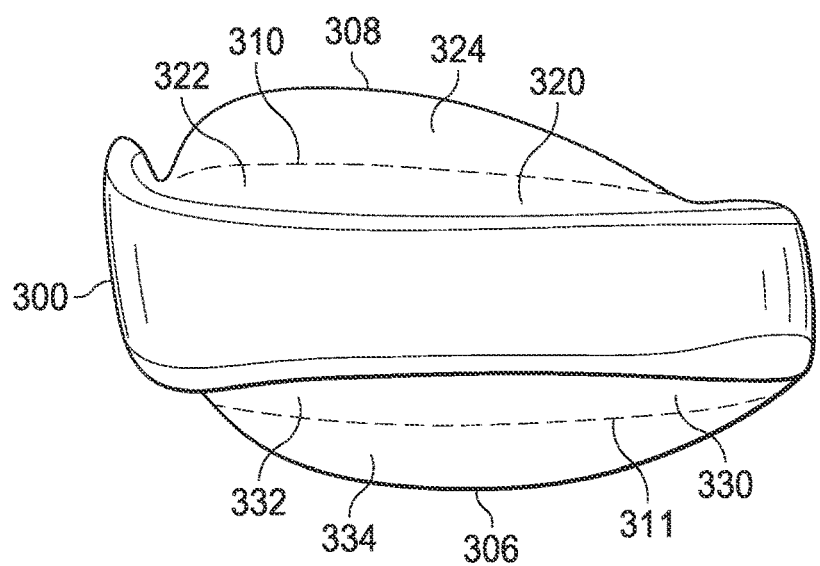
Figure 21B:
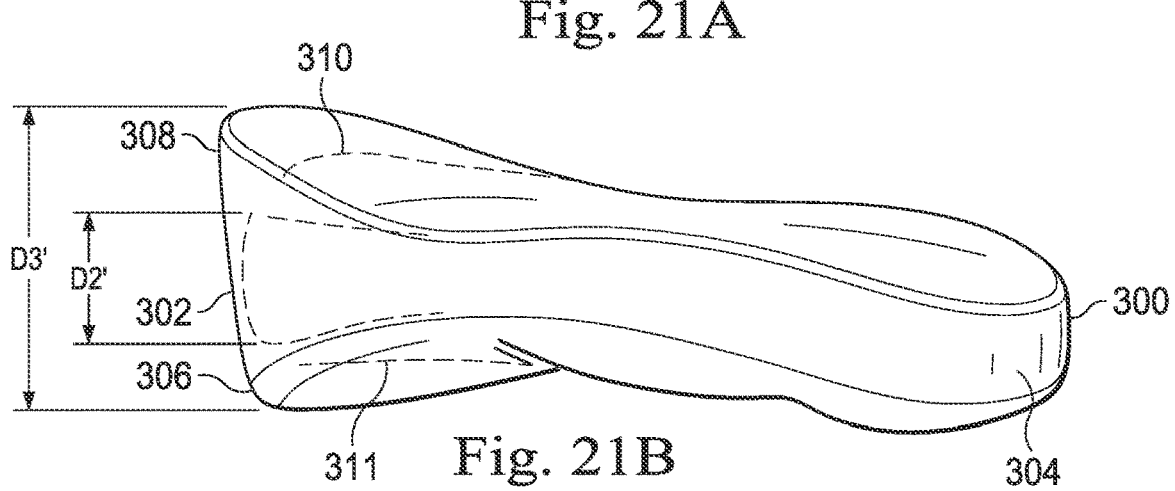

Referring now to FIGS. 21A and 21B, additional details of the extensions 306 and 308 are shown. More specifically, lower extension 306 includes a tibial plateau surface 330 having a first portion 332 above the dashed line 311 and a second extension portion 334. The upper extension 308 includes a femur surface 320 having a first portion 322 below the dashed line 310 and a second extension portion 324. The distance D2' between the dashed lines 310 and 311 is approximately 6 mm. The distance D3' between the inferior most portion of extension 306 and the superior extension 308 is approximately 12-18 mm. As will be appreciated, for the illustrated embodiment, the posterior end wall as a height of approximately 9.0 mm. Thus, the anterior anti-migration structure 302 has a height that is about two times the height of the posterior end of the implant.

In some embodiments, the prosthetic device is a melt mold composite implant composed of two biocompatible materials: DSM Bionate® Polycarbonate-Urethane (PCU), 80 Shore A, matrix material and ultra high molecular weight polyethylene (UHMWPE) reinforcement material (Dyneema Purity). In some particular embodiments, a prosthetic device formed of PCU and reinforced circumferentially with DSM Dyneema® fibers results in a desirable distribution of loads on the underlying articulation surfaces of the prosthetic device. Accordingly, referring generally to FIGS. 22-24 aspects and methods of manufacturing such a device will be described.

Figure 22:
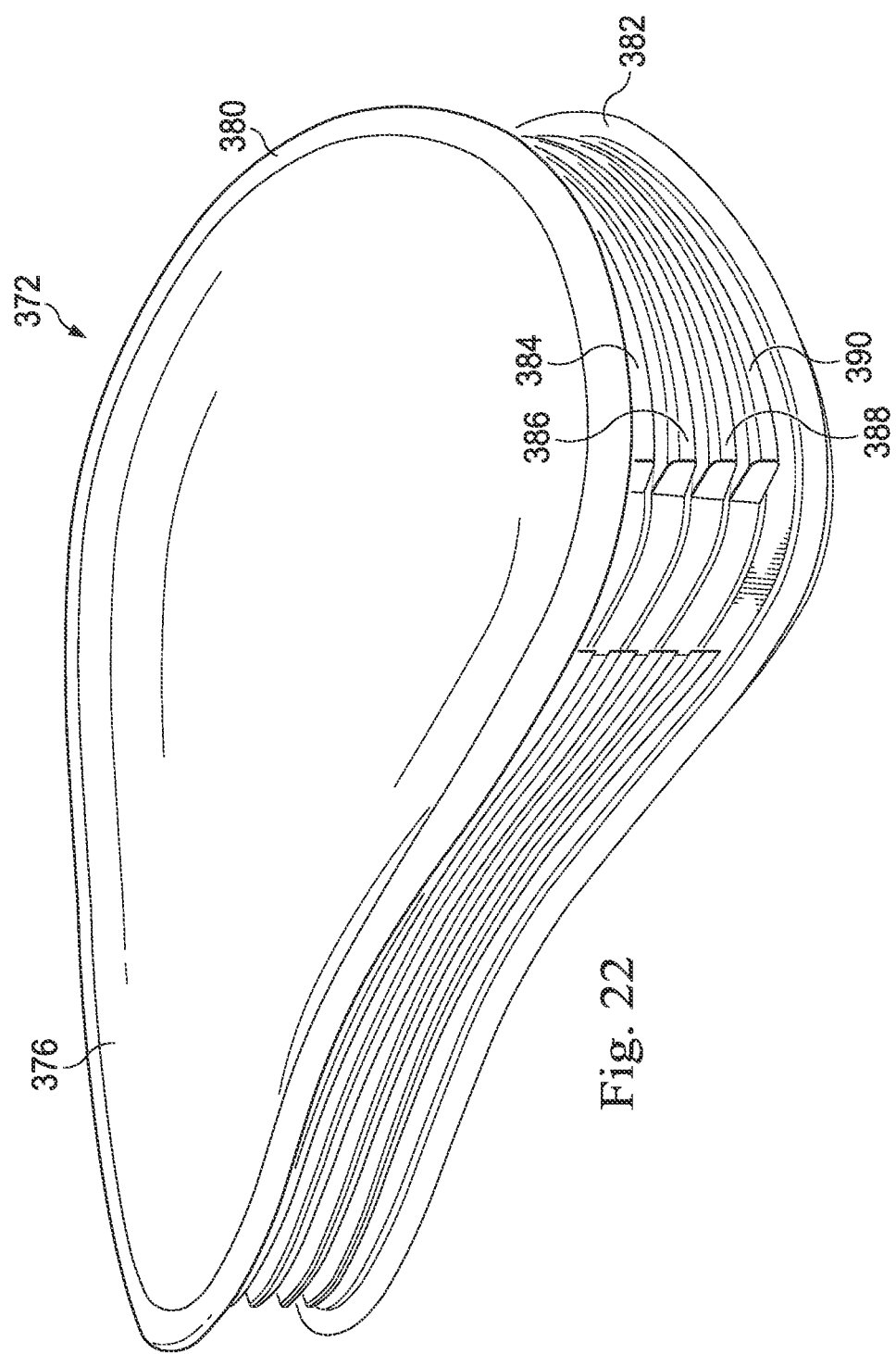

Referring more specifically to FIGS. 22 and 23, shown therein is a prosthetic device core 372 surrounded by an outer portion 436. The prosthetic device core 370 includes an upper articulation surface 376 and an opposing lower articulation surface 378. The upper articulation surface 376 is configured to engage the femur while the lower articulation surface 378 is configured to engage the tibia. In some embodiments, the prosthetic device core 372 is formed via an injection molding process that substantially limits the defects, imperfections, and/or process residue in and on the articulation surfaces. In that regard, the articulation surfaces may obtain a smoothness substantially similar to that of the surfaces of the mold in which they are formed. In some instances, the mold surfaces are mirror polished to an optical polish between about 0.05 Ra and 0.4 Ra.

The prosthetic device 370 is imbedded with fibers shown in FIG. 24. In some instances, the fibers are positioned circumferentially around the prosthetic device core 372. In that regard, the core 372 includes features to facilitate positioning of the fibers within the prosthetic device 370 in some embodiments. For example, referring more specifically to FIG. 23, shown therein is a diagrammatic perspective view of the core 372 according to one aspect of the present disclosure. As shown, the core 372 includes an upper rim 380 and a lower rim 382 defining an outer boundary of the core. Between the upper and lower rims 380, 382 the core 372 includes a series of alternating projections and recesses. In the current embodiment, the core includes projections 384, 386, 388, and 390 between the upper rim 380 and the lower rim 382. Between the rims 380, 382 and the projections the core 372 includes recesses 392, 394, 396, 398, and 400. In some embodiments, the recesses 392, 394, 396, 398, and 400 are sized and shaped to receive the fibers to be imbedded within the device 370. In some instances, the projections 384, 386, 388, 390 and the recesses 392, 394, 396, 398, 400 are configured such that the fibers may be wound around the core 372.

As shown in FIG. 23, a tether loop 450 is shown positioned between the core 372 and the reinforcing fibers 452. During the manufacturing process, one or more loops 450 are positioned adjacent the core 372 and maintained there while one or more reinforcing fibers are wound circumferentially around the core. As shown in FIG. 24, after the over-flow molding process is completed, the reinforcing fibers 438 and a portion of the suture loop 452 are encapsulated into the prosthetic implant. As a further alternative, it can be one or more continuous fibers that go in toward the core and back out again to form external loops at different locations along the exterior of the implant.

In some embodiments, the fibers are configured to distribute the load across the prosthetic device 370 in a manner that mimics a natural meniscus. In that regard, the amount of fibers, the type of fibers, distribution of the fibers, and/or the location of the fibers is altered in some embodiments to achieve a desired load distribution. Further, these attributes of the fiber may vary within a single implant depending on the position within the implant. For example, in some instances the number or density of fibers varies along the height of the prosthetic device. In some instances, the fiber characteristics are determined at least partially based on the patient receiving the prosthetic device 370. For example, factors such as the size of the patient's knee anatomy, the patient's weight, the patient's anticipated activity level, and or other aspects of the patient are taken into consideration when determining the characteristics of the fibers imbedded in the prosthetic device 370. In some instances, a fiber incorporation ratio (FIR) is taken into consideration. Generally, the fiber incorporation ratio is representative of the amount or percentage of fibers within the prosthetic device 370 as compared to the matrix material or base material. In some embodiments, the fiber incorporation ratio is measured as the area of the fibers divided by the area of the prosthetic device as view in a cross-section of the device, or $$FIR = \frac{\text{Area}_{FiberCS}}{\text{Area}_{DeviceCS}}.$$

In some embodiments, the resilient matrix material comprises a biocompatible polymer. In some instances, the polymer is a polycarbonate polyurethane. In one specific embodiment, the matrix material is DSM Bionate® Polycarbonate-Urethane (PCU), 80 Shore A. The high modulus reinforcement material utilized in the application may be any one of the following: Ultra High Molecular Weight Polyethylene (UHMWPE) fiber, for example DSM Dyneema® Purity; Para-aramid synthetic fiber, for example DuPont™ Kevlar, Kevlar29, Kevlar49; carbon; stainless-steel; titanium; nickel-titanium (Nitinol); and/or other suitable reinforcement materials. In that regard, the fibers may be employed in a monofilament or multifilament form as a single strand or a multiple fiber twine, in a diameter range of up to 1 mm.

Figure 25A:
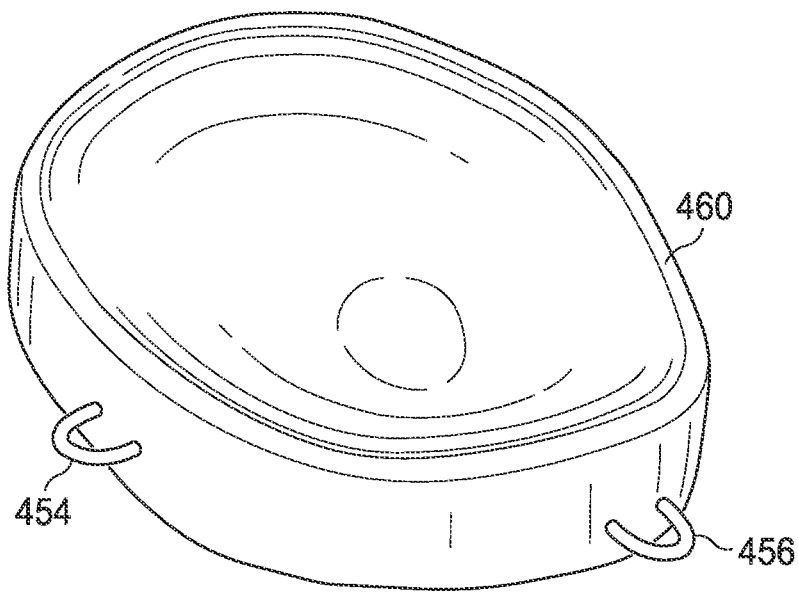
FIGS. 25A and 25B are diagrammatic perspective views of a left medial meniscus implant having tethering loops.
Figure 25B:
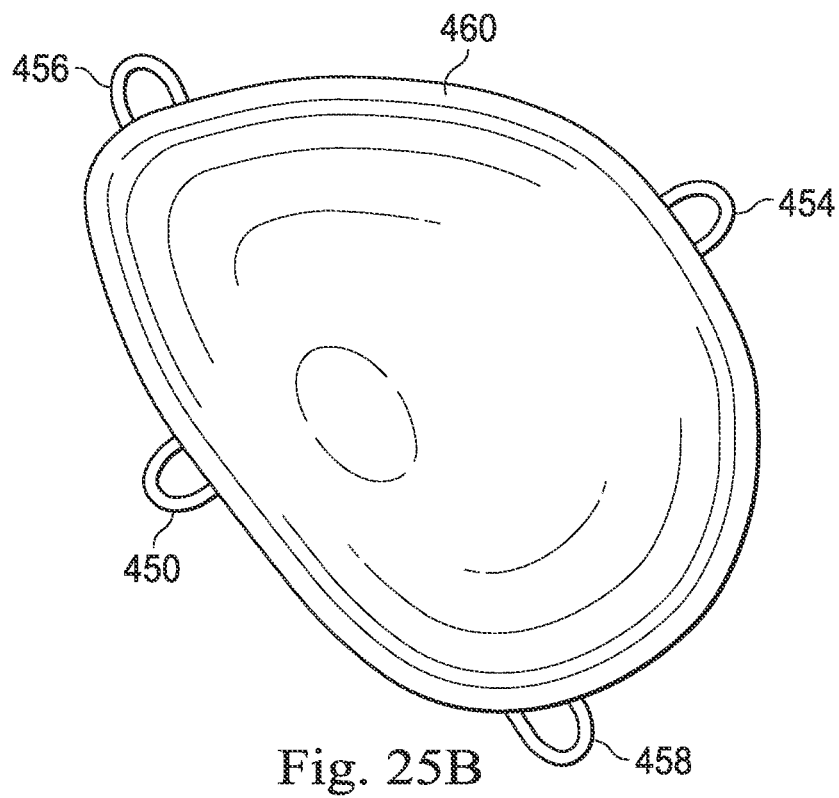

Referring now to FIGS. 25A and 25B, there is shown a further embodiment of a meniscus replacement device 460 according to another aspect of the present disclosure. The implant 460 includes tethering loops 450, 454, 456 and 458. The loops are formed by a series of fibers loosely wound around the core 372 after the tension elements discussed with respect to FIGS. 22 and 23 are positioned, with slack portions held outwardly during the over-flow molding process to form the loops shown in FIG. 25B. Thus, in one form, the loops 450, 454, 456 and 458 are formed of a series of filaments that are partially embedded within the over molded area and partially extending beyond the sidewalls. The loops themselves may also include a coating of the over molding material. In one form, each loop has a unique set of filaments extending around the core 376 (FIG. 23) such that if one loop is cut off, severing of the fibers will not impact the remaining loops. In still a further form, one or more fiber reinforced tabs extend outwardly from the outer side wall. Although the tabs lack a preformed opening, the tabs provide fiber reinforced areas for the passage of a needle and suture that can firmly retain the suture without damaging the pliable material of the implant. In one aspect, the tabs are spaced around the implant at strategic locations similar to FIG. 25B, while in another form, the fiber reinforced tab extends completely around the side wall perimeter of the implant.

Figure 26:
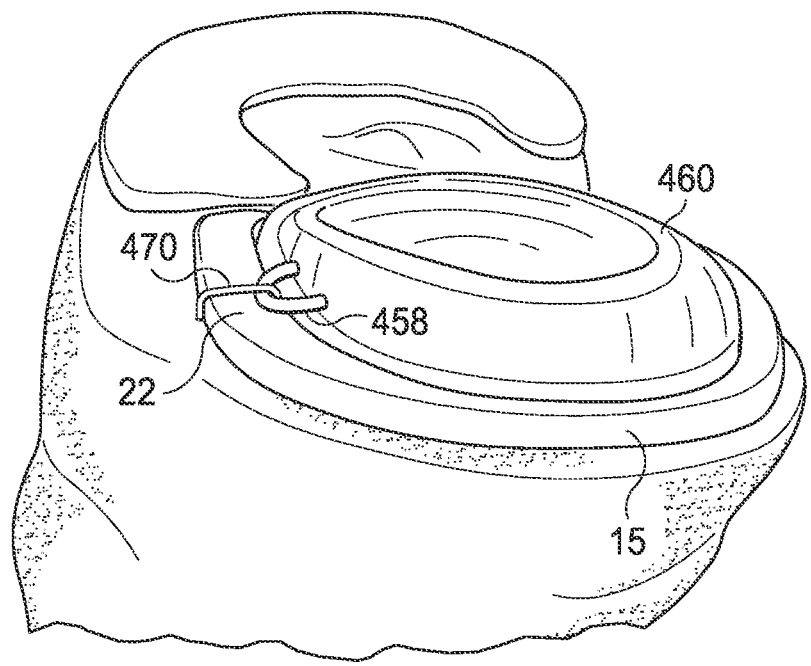
FIGS. 26-28 are diagrammatic illustrations showing implantation of a right medial meniscus replacement device including tethering loops.
Figure 27:
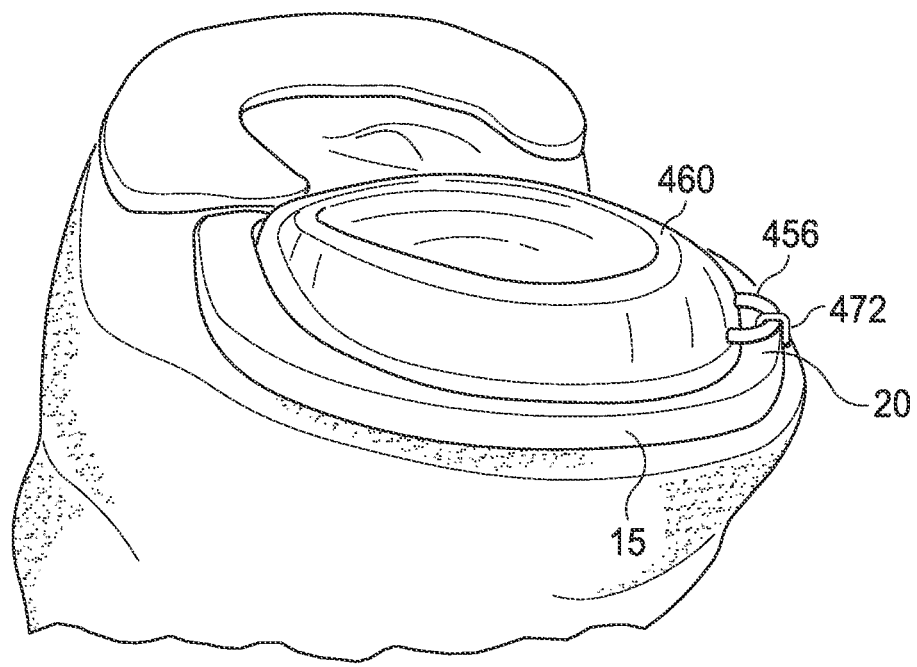

In use, the implant 460 can be inserted into the joint space in a conventional fashion. As shown in FIG. 26, the anterior tethering loop 458 is positioned adjacent the anterior rim 22 and a suture 470 is passed through the loop 458 and the anterior rim 22. The tension applied to the suture can be varied to provide the correct amount of freedom of movement within the joint space. The other tether loops that are not used can be severed by the physician before implantation in the joint space. Referring now to FIG. 27, the implant 460 is positioned in the spaced formed within the remaining portions of the meniscus 15 with the tethering loop 456 positioned adjacent the posterior rim 20. A suture is passed through the loop 456 and the posterior rim 20 to maintain the implant within the joint space. In both the tethering arrangements of FIGS. 26 and 27, the implant 460 has a high degree of freedom of movement with the joint space such that the implant retains its ability to float freely within the joint to mimic a natural meniscus. In still a further aspect, the one or more tether loops 454, 456 and 458 are attached to the soft tissue of the joint capsule.

Figure 28:
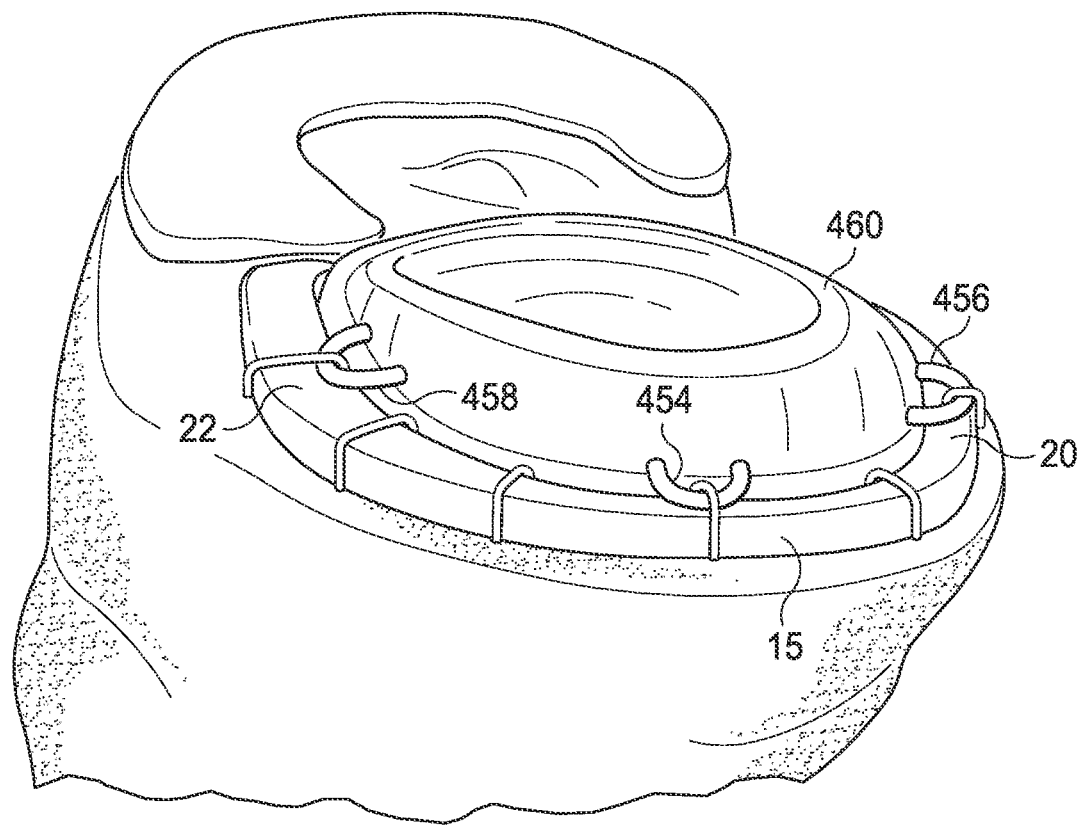

Referring now to FIG. 28, the implant 460 is more fully tethered in the joint space by a suture that extends through all or part of the tether loops 454, 456 and 458 and around the meniscus rim 15 including the posterior rim 20 and the anterior rim 22. In this arrangement, the implant 460 is constrained to a more limited zone of movement providing a limited range of motion.

Figure 29:
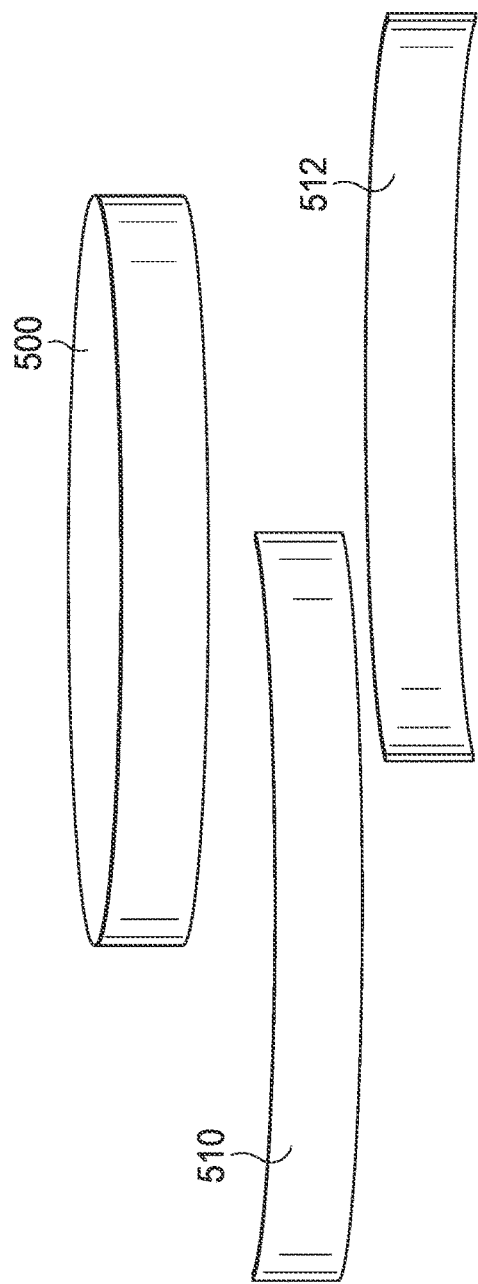
FIGS. 29-31 illustrate a radiopaque trialing assembly associated with a meniscus replacement device.
Figure 30:
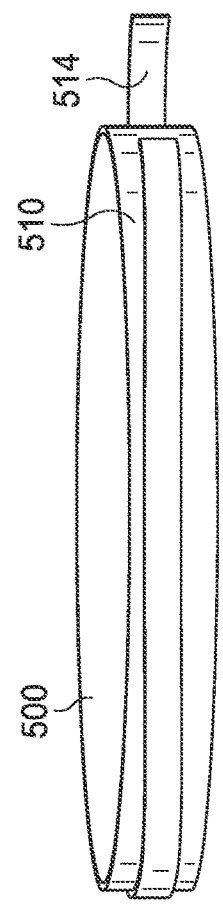
Figure 31:
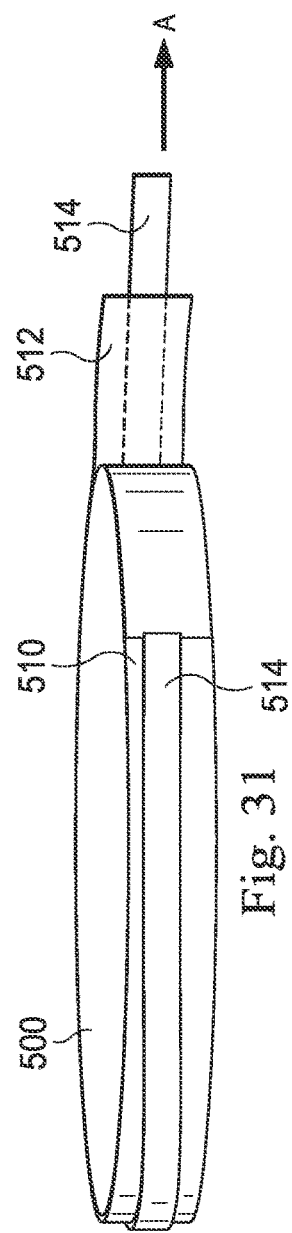
Figure 32B:
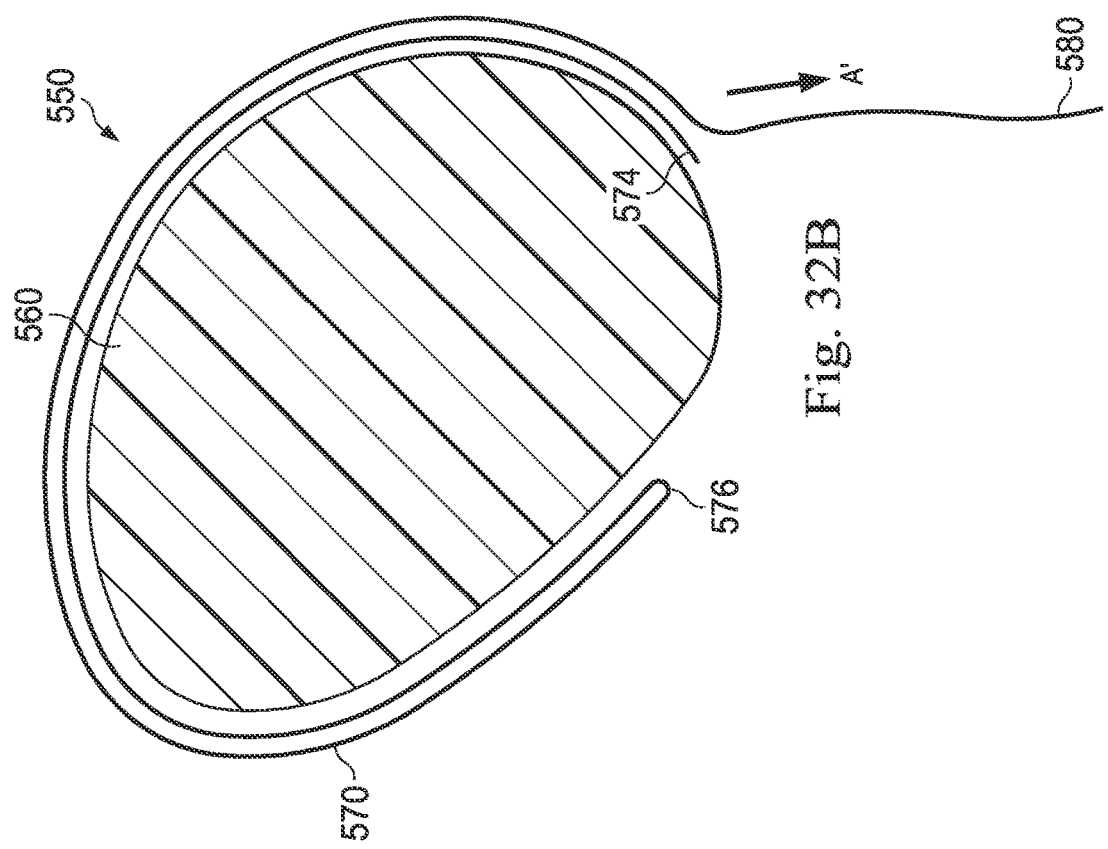
FIGS. 32A and 32B illustrate a further radiopaque trialing assembly associated with a meniscus replacement device.
Figure 32A:
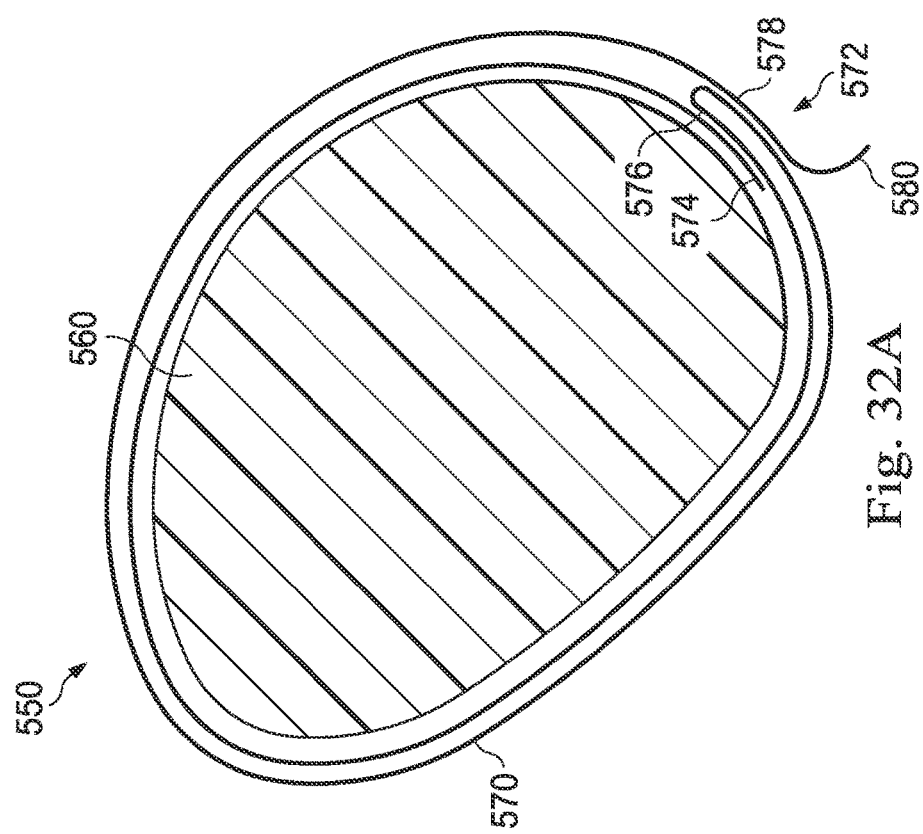

Referring now to FIG. 29, there is shown a diagrammatically illustration of an implant 500 similar to those described above in combination with a pair of radiopaque films 510 and 512 having a width approximating the thickness of the implant. Such film may include a radiopaque material incorporated into a polymer or other material. The radiopaque material can include for example, barium sulfate at a 10-30% ratio combined in a polymer matrix. The radiopaque films can be positioned on the circumference of the implant 500. As shown in FIG. 30, an adhesive strip 514 can be circumferentially wrapped around the radiopaque films to maintain them in position on the implant during implantation. As can be appreciated, the implant with the radiopaque films can be implanted into the joint space. The knee can be moved through a range of motion and the implant monitored by radiographic imaging to determine its positioning in the joint space and whether it will successfully meet the patient's needs. Once a determination is made that the implant is satisfactory, an end of the adhesive 514 is peeled from the overlap area. Once the end is free, continued movement in the direction of arrow A will pull the radiopaque films 510 and 512 from around the implant and out of the body. In an alternative embodiment 550 illustrated in FIGS. 32A and 32B, a radiopaque film or band 570 is double circled around the implant 560 with a loop 576 after the first encirclement of the film. A first end 574 of the radiopaque band 570 is positioned against the implant 560 and overlapped by at least a portion of the loop 576. A second end 580 is passed back around the implant 560 to define an area of overlap area 572 where portion 578 extends over the loop 576. Engagement between the loop and portion 578 in the area of overlap 572, along with engagement between the first portion 574 and the loop 576, retains the band in position. The engagement areas can rely on friction, adhesive or a separate suture or filament to retain the loop and band overlap areas in contact. Although the radiopaque band 570 is shown in a loose configuration for the ease of illustration, it will be appreciated that in most embodiments, the band will be tightened around the outer wall perimeter of the implant 560. In use, the implant assembly 550 is positioned in the knee joint. Once a determination is made that the implant is satisfactory, the end 580 is pulled in the direction of arrow A' to release the adhesive or other retention mechanism to peel the band from the overlap area 572. Once the end 580 is free, continued movement in the direction of arrow A' will pull the radiopaque film 570 from around the implant and out of the body.

Figure 33A:
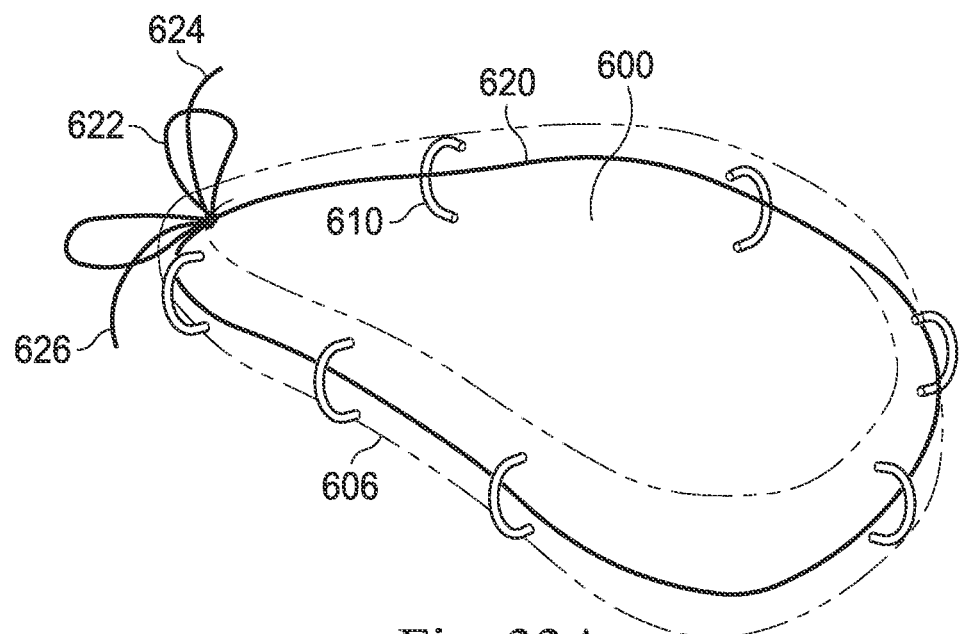
FIGS. 33A and 33B illustrate a still further radiopaque trialing assembly associated with a meniscus replacement device.
Figure 33B:
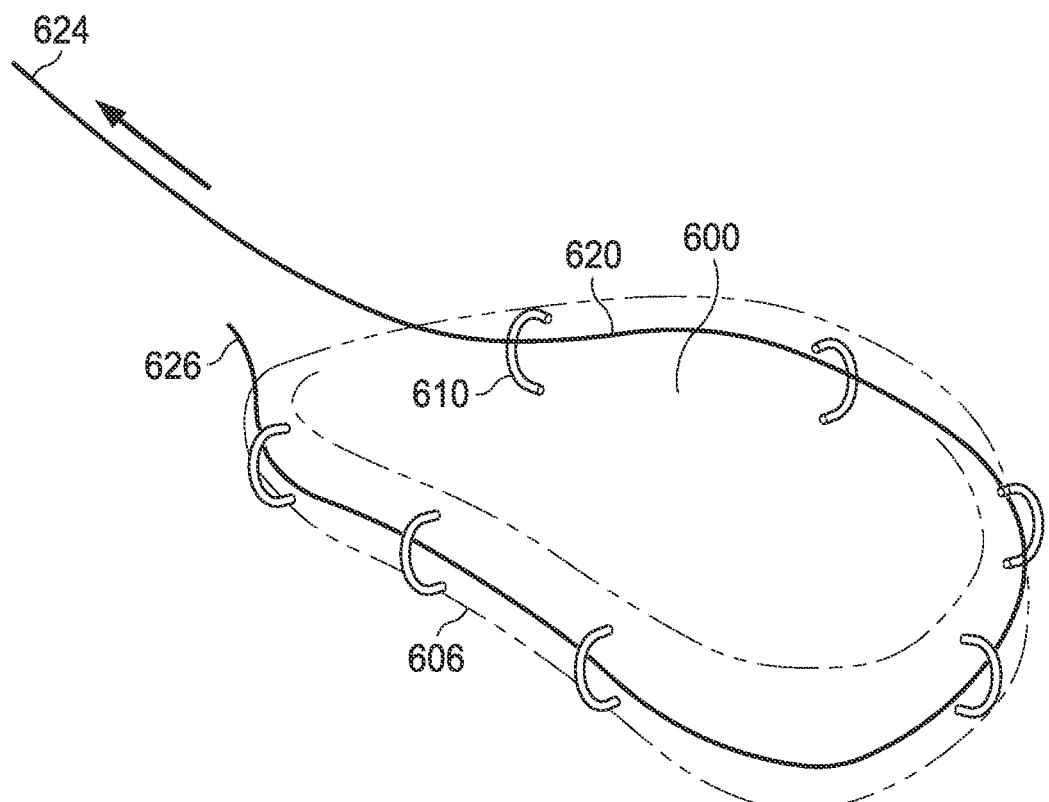

Referring now to FIGS. 33A and 33B, there is shown still a further embodiment according to another aspect of the present disclosure. The implant 600 has the superior surfaces and retention features discussed above along with a series of tether loops 610. As illustrated, the loops 610 are positioned around the perimeter 606 of the implant 600 with the loops aligned from the top to the bottom of the implant, similar to the embodiments shown in FIGS. 23 and 24 such that the openings along the sides of the loops are oriented generally along the longitudinal axis. A radiopaque filament 620, such as a wire or thread, is threaded through the loops 610 to extend around the perimeter of the device. Radiopaque wires may be formed of or include precious metals, stainless steel, titanium, or nitinol. The filament 620 is tied in a knot 622 to retain the position of the filament on the implant 600 during implantation. Although a knot is shown, other releasable fixation mechanisms can be used to retain the filament in position. During use, the implant 600 and filament 620 combination is inserted into the joint. The joint is moved through a range of motion and the implant filament 620 is monitored via radiographic imaging to determine if the implant is performing the desired function. If the implant 600 is the proper match for the patient, the knot 622 is undone, and end 624 pulled until the terminal end 626 is removed from the loops 610. In the illustrated embodiment, the loops 610 may be used for tethered anchoring, may be left intact, or may be cut before final implantation. In this manner, the final implant can also serve as a trial device allowing the physician to evaluate the implant performance before final implantation.

Although loops 610 are illustrated as extending outwardly beyond the sidewall of the implant 600 to define an intermittent passage around the perimeter 606 of the implant, it is contemplated that in an alternative form a channel can be formed in the sidewall of the implant 600 during the molding process to provisionally retain the filament 620 in position.

Although described in the context of a knee meniscus, the composite implants described above may be utilized for forming a variety of prosthetic devices. For example, in some instances the composite implants are utilized for knee joints (including meniscus and total knee joints), hip joints (including acetabular cups), shoulder joints, elbow joints, finger joints, and other load and/or non-load receiving prosthetic devices. Still further, while embodiments were disclosed with certain features on anterior and/or posterior portions, it is contemplated that features from one embodiment, such as a unique anterior feature, may be combined with an alternative posterior feature design to create a composite implant embodying both the above described anterior and posterior features from one or more of the implants described above.

It should be appreciated that in some instances the prosthetic devices of the present disclosure are formed by other processes than those described herein. These manufacturing processes include any suitable manufacturing method. For example, without limitation any of the following manufacturing methods may be utilized: injection molding including inserting inserts; compression molding including inserting inserts; injection-compression molding including inserting inserts; compression molding of prefabricated elements preformed by any of the above methods including inserting inserts; spraying including inserting inserts; dipping including inserting inserts; machining from stocks or rods; machining from prefabricated elements including inserting inserts; and/or any of the above methods without inserts. Further, it should be appreciated that in some embodiments the prosthetic devices of the present disclosure are formed of medical grade materials other than those specifically identified above. In that regard, in some embodiments the prosthetic devices are formed of any suitable medical grade material.

While the principles of the present disclosure have been set forth using the specific embodiments discussed above, no limitations should be implied thereby. Any and all alterations or modifications to the described devices, instruments, and/ or methods, as well as any further application of the principles of the present disclosure that would be apparent to one skilled in the art are encompassed by the present disclosure even if not explicitly discussed herein. It is also recognized that various presently unforeseen or unanticipated alternatives, modifications, and variations of the present disclosure may be subsequently made by those skilled in the art. All such variations, modifications, and improvements that would be apparent to one skilled in the art to which the present disclosure relates are encompassed by the following claims.

What is claimed is:

1. A prosthetic meniscus device for placement in a knee joint, the prosthetic meniscus device having a substantially ellipsoidal shape and comprising:
   a central portion having an upper femur-contacting surface for engagement with a portion of a femur and an opposing lower tibial-contacting surface for engagement with a portion of a tibia, the central portion comprising a resilient material;
   an outer portion surrounding the central portion and having an increased thickness relative to the central portion, the outer portion comprising a resilient material with a reinforcement material embedded in the resilient material of the outer portion, the reinforcement material comprises at least one fiber disposed circumferentially around the central portion,
   wherein the outer portion further comprises a retention structure sized and shaped to prevent posterior migration of the prosthetic meniscus device in the knee joint,
   wherein the retention structure comprises a pocket formed on a posterior sidewall of the outer portion and sized to receive a posterior remnant of the meniscus,
   wherein the pocket is disposed between a posteriorly extending inferior portion of the posterior sidewall and a vertically extending superior portion of the posterior sidewall,
   wherein the posteriorly extending inferior portion is oriented in a lateral direction and the vertically extending superior portion is oriented in a superior-inferior direction such that the posteriorly extending inferior portion and the vertically extending superior portion are substantially perpendicular to one another,
   wherein the pocket comprises a concave shape defined at least in part by a superior surface of the posteriorly extending inferior portion and a side-facing surface of the vertically extending superior portion,
   wherein the posteriorly extending inferior portion defines a plow blade shape configured to slide under at least a portion of the posterior remnant,
   wherein the posteriorly extending inferior portion comprises a leading lower edge and the vertically extending superior portion comprises an upper edge,
   wherein the leading lower edge extends further posteriorly than the upper edge,
   wherein the retention structure is configured to inhibit extreme movement of the prosthetic meniscus device within the knee joint while permitting free floating of the prosthetic meniscus device over a significant range.

2. The device of claim 1, wherein the leading lower edge extends further posteriorly than the upper edge by approximately 5 mm.

3. The device of claim 1, wherein the retention structure further comprises an enlarged anterior flange configured to engage an anterior portion of at least one of a tibia or a femur in the knee joint to inhibit the posterior migration.

4. The device of claim 3, wherein the anterior flange has a height that is at least 30 percent greater than a posterior height of the prosthetic meniscus device.

5. The device of claim 1, wherein the retention structure further comprises one or more tethering extensions extending from the outer portion of the prosthetic meniscus device.

6. The device of claim 5, wherein the tethering extensions are loops.

7. The device of claim 5, wherein the tethering extensions are fiber reinforced tabs.

* * * * *